(12) United States Patent
Winn

(10) Patent No.: US 6,307,121 B1
(45) Date of Patent: Oct. 23, 2001

(54) BACTERIOPHAGE-BASED TRANSGENIC FISH FOR MUTATION DETECTION

(75) Inventor: Richard N. Winn, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/322,725

(22) Filed: May 28, 1999

Related U.S. Application Data
(60) Provisional application No. 60/087,430, filed on May 31, 1998.

(51) Int. Cl.$^7$ ............... G01N 33/00; A01K 67/027; C12N 15/00; C07H 21/02; C07H 21/04
(52) U.S. Cl. ............... 800/3; 800/20; 800/21; 800/25; 536/23.1; 536/23.7
(58) Field of Search ............... 800/3, 20, 21, 800/25, 18; 536/23.1, 23.5, 23.7

(56) References Cited

U.S. PATENT DOCUMENTS

| | | | |
|---|---|---|---|
| 5,347,075 | 9/1994 | Sorge | 800/18 |
| 5,470,706 | 11/1995 | Vijg et al. | 435/6 |
| 5,510,099 * | 4/1996 | Short | 424/9.2 |
| 5,545,808 * | 8/1996 | Hew et al. | 800/20 |
| 5,589,155 | 12/1996 | Sorge et al. | 424/9.2 |
| 5,602,300 | 2/1997 | Gossen et al. | 800/18 |
| 5,817,290 | 10/1998 | Vijg et al. | 424/9.2 |
| 5,824,287 | 10/1998 | Sorge et al. | 424/9.2 |
| 6,114,600 * | 9/2000 | Ow et al. | 800/278 |

FOREIGN PATENT DOCUMENTS

| | | |
|---|---|---|
| 289121 B1 | 11/1988 | (EP) . |
| 353812 B1 | 2/1990 | (EP) . |
| 08205708 | 1/1965 | (JP) . |
| 96029093 B2 | 3/1996 | (JP) . |
| 8205708 | 8/1996 | (JP) . |
| 2618973 | 3/1997 | (JP) . |
| 9100567 | 11/1992 | (NL) . |
| 8801826 | 2/1998 | (NL) . |
| WO 00/24246 | 5/1960 | (WO) . |
| WO 91/15579 | 10/1991 | (WO) . |
| WO 92/17605 | 10/1992 | (WO) . |
| WO 93/15769 | 8/1993 | (WO) . |
| WO 93/17123 | 9/1993 | (WO) . |
| WO 96/37579 | 11/1996 | (WO) . |
| WO 97/05484 | 2/1997 | (WO) . |
| WO 99/62333 | 12/1999 | (WO) . |

OTHER PUBLICATIONS

DuBridge et al., "Recombinant Shuttle Vectors for the Study of Mutation in Mammalian Cells," *Mutagenesis*, 3(1):1–9 (1988).

Hinton et al., "Cytological Changes During Progression of Neoplasia in Selected Fish Species," *Aquat. Toxicol.*, 11:77–112 (1988).

Bearzotti et al., Gene expression following transfection of fish cells, Nov. 1992, Journal of Biotechnology, vol. 26, pp. 315–325.*

Winn et al., Transfer, Methylation and Spintaneous Mutation . . . , 1995, Marine Environmental Research, vol. 40, No. 3, pp. 247–265.*

Article: "Scientists fish for toxicity clues", *Chemistry & Industry*, pp. 131 (1999).

Bayer et al., "A Transgene Containing lacZ is Expressed in Primary Sensory Neurons in Zebrafish," *Development*, 115:421–426 (1992).

Boerrigter et al., "Plasmid–based transgenic mouse model for studying in vivo mutations", *Nature*, 377 (6550):657–659 (1995).

Boerrigter et al., "Sources of Variability in Mutant Frequency Determinations in Different Organs of lacZ Plasmid–based Transgenic Mice: Experimental Features and Statistical Analysis", *Env. Mol. Mutagenesis*, 29(3):221–229 (1997).

Boerrigter, "High Sensitivity for Color Mutants in lacZ Plasmid–Based Transgenic Mice, as Detected by Positive Selection", *Env. Mol. Mutagenesis*, 32(2):148–154 (1998).

Culp et al., "High–frequency germ–line transmission of plasmid DNA sequences injected into fertilized zebrafish eggs", *Proc. Natl. Acad. Sci. USA*, 88(18):7953–7957 (1991).

Detrick, "Transgenic Fish Model for Mutagenicity Testing", Crisp Data Base National Institute of Health, located at website: alt1.csa.com/htbin/ids51/procskel.cgi, Abstract, 1 pg. (1994).

Dolléet al., "Evaluation of a plasmid–based transgenic mouse model for detecting in vivo mutations", *Mutagenesis*, 11(1):111–118 (1996).

Douglas et al., "Sequence spectra of spontaneous lacZ gene mutations in transgenic mouse somatic and germline tissues", *Mutagenesis*, 9(5):451–458 (1994).

Driever et al., "A genetic screen for mutations affecting embryogenesis in zebrafish", *Development*, 123:37–46 (1996).

(List continued on next page.)

Primary Examiner—Deborah J. R. Clark
Assistant Examiner—Shin-Lin Chen
(74) *Attorney, Agent, or Firm*—Mueting, Raasch & Gebhardt, P.A.

(57) ABSTRACT

The present invention provides transgenic fish whose somatic and germ cells contain a genomically integrated bacteriophage lambda-derived transgene construct. The transgene construct can include an excisable test nucleic acid sequence containing a heterologous mutation target nucleic acid sequence that is detectable via bioassay in a bacterial cell into which the test nucleic acid has been introduced. The frequency of mutations in the mutation target nucleic acid sequence following exposure of the transgenic fish to one or more potentially mutagenic agents can thus be evaluated.

35 Claims, 4 Drawing Sheets

OTHER PUBLICATIONS

Fosgate, Ed., "Fish may soon replace lab mice", *Forresters' Log*, pp. 6 and pp. 8 (1999).

Fosgate, "Transgenic fish may give lab mice a day off", *Georgia Magazine*, pp. 11 (1999).

Gossen et al., "Plasmid Rescue from Transgenic Mouse DNA Using LacI Repressor Protein Conjugated to Magnetic Beads", *BioTechniques,* 14(4):624–629 (1993).

Gossen et al., "Spontaneous and X–ray induced deletion mutations in LacZ plasmid–based transgenic mouse model" *Mut. Res.,* 331:89–97 (1995).

Lin et al., "lacZ Expression in Germline Transgenic Zebrafish Can Be Detected in Living Embryos," *Developmental Biology,* 161:77–83 (1994).

Riley et al., "Efficient induction of point mutations allowing recovery of specific locus mutations in zebrafish", *Proc. Natl. Acad. Sci. USA,* 92(13):5997–6001 (1995).

Rü ther et al., "Easy identification of cDNA clones", *EMBO J.,* 2(10):1791–1794 (1983).

Solnica–Krezel et al., "Efficient Recovery of ENU–Induced Mutations From the Zebrafish Germline", *Genetics,* 136:1401–1420 (1994).

Stuart et al., "Replication, integration and stable germ–line transmission of foreign sequences injected into early zebrafish embryos", *Development,* 103(2):403–412 (1988).

Susman, "Gene–altered fish check new chemicals", located at website: news.chemicalonline.com/wires/19990124–421734772.htm, 2 pgs. (1999).

Tao et al., "Comparison of somatic mutation in a transgenic versus host locus", *Proc. Natl. Acad. Sci., USA,* 90(22):10681–10685 (1993).

Torassa, "Animals Hold Key to Cures", located at website: abcnews.go.coM:80/sections/science/DailyNews/scorpions9990125.htm, 2 pgs. (1999).

Vijg, et al., "Ch.29: Bacteriophage Lamda and Plasmid lacZ Transgenic Mice for Studying Mutations in vivo", *Technologies for Detection of DNA Damage and Mutations,* Plenum Press, NY, Title page, publication page, table of contents and pp. 391–410 (1996).

Winn et al., "Detection of mutations in transgenic fish carrying a bacteriophage λcii transgene target", *PNAS,* 97(23):12655–12660 (2000).

"MutaPlax™ Transgenic Lambda DNA Packaging System," [online] [retrieved May 7, 1998]. Retrieved from the Internet: interscience.com/epicentre/mutplxc2.html, 1 page.

"MutaPlax cII—Select™ Packaging and Selection Kit," [online] [retrieved May 28, 1998]. Retrieved from the Internet: interscience.com/epicentre/mutplxc2.html, 1 page.

"A short description of the lambda cII system," [online]. Biology Dept., University of Victoria, Canada, [retrieved on May 8, 1998]. Retrieved from the Internet darwin.ceh.uvic.ca/bigblue/cci–info.htm, 1 page.

Amanuma et al. Transgenic Zebrafish for Detectig Mutations Caused by Compounds in Aquatic Environments. Nature Biotechnology, vol. 18, pp. 62–65, Jan. 2000.*

Murray, J.D. et al. Transgenic Animals in Agriculture. CABI Publishing. New York, 1999.*

Houdebine, L.M. et al. Transgenesis in Fish. Experientia 47(9): 891–897, Sep. 1991.*

Liu, Z. et al. Development of Expression Vectors for Transgenic Fish. Bio/Technology 8:1268–1272, Dec. 1990.*

Lubzens, E. et al. Cryopreservation as a tool in aquaculture. Israeli Journal of Aquaculture 44(4):137, 1992.*

Bailey et al., "Initiation, Promotion, and Inhibition of Carcinogenesis in Rainbow Trout," *Environ. Health Perspect.* 71:147–153 (1987).

Barnes, "Fish Embryonal Stem Cells for Development of Transgenics", Abstract, Grant No. 5 R01 ES06011–06, 1 pg. (no later than Mar. 1998).

Black, "Aquatic Animal Neoplasia as an Indicator for Carcinogenesis Hazards to Man," *Hazard Assessment of Chemicals: Current Developments* vol. 3, Saxena, ed., Academic Press, New York. 181–232 (1984).

Burkhart et al., "Non–Mammalian and Environmental Sentinels in Human Health: Back to the Future?" *Human and Ecological Risk Assessment* vol. 3, CRC Press LLC, 309–328 (1997).

Burkhart et al., "Spontaneous and Induced Mutagenesis in Transgenic Animals Containing φX174," *Environ. Mol. Mut.* 21:8–9 Abstract Only (1993).

Burkhart et al., "ENU–induced Mutagenesis at a Single A : T Base Pair in Transgenic Mice Containing φX174," *Mutation Res.* 292:69–81 (1993).

Burkhart, "Comparative Mutagenesis in Aquatic Models, Rodents, and Cells in Culture," Abstract, Grant Z01 ES21187–02, 1 pg. (no later than Mar. 1998).

Chen, "Transgenic Fish a Model for Environmental Toxicology," Abstract, Grant No. 5 R01 RR11680–03, 1 pg. (no later than Mar. 1998).

Driever et al., "Zebrafish: Genetic Tools for Studying Vertebrate Development," *Trends Genet.* 10(5):152–159 (1994).

Dycaico et al., "The Use of Shuttle Vectors for Mutation Analysis in Transgenic Mice and Rats," *Mutation Res.* 307:461–478 (1994).

Gallagher et al., "A Comparative Approach to 7,12–Demethylbenz[A] Anthracene Effects: Metabolism and Mutagenesis in Mice and Fish," *Environ. Mol. Mut.* 29:15–16, Abstract Only (1997).

Goldsworthy et al., "Transgenic Animals in Toxicology," *Fund Appl. Toxicol.* 22:8–19 (1994).

Gossen et al., "Efficient Rescue of Integrated Shuttle Vectors from Transgenic Mice: A Model for Studying Mutations In Vivo," *Proc. Natl. Acad. Sci.* 86:7971–7975 (1989).

Grunwald, "Embryo Stem Cell Cultures and Gene Transfer in Zebrafish," Abstract, Grant No. 5 R01 RR10253–04, 1 pg. (no later than Mar. 1998).

Gu et al., "Development of a λ–based Complementation Assay for the Preliminary Localization of lacI mutants from the Big Blue ™ Mouse: Implications for a DNA–Sequencing Strategy," *Mutation Res.* 307:533–540 (1994).

Guyomard et al., "Integration and Germ Line Transmission of Foreign Genes Microinjected into Fertilized Trout Eggs," *Biochemic,* 71:857–863 (1989).

Hawkins et al., "Carcinogenicity Tests Using Aquarium Fish," *Fundamentals of Aquatic Toxicology: Effects, Environmental Fate, and Risk Assessment,* Chapter 14 in G.M. Rand, ed., Taylor and Francis, 421–446 (1995).

Hendricks, "Chemical Carcinogenesis in Fish," *Aquatic Toxicology,* Weber, ed., Raven Press, New York., 149–211 (1982).

Inoue et al., "Stage–dependent Expression of the Chicken δ–crystallin Gene in Transgenic Fish Embryos," *Cell Differ. Dev.* 27(1):57–68 (1989).

Inoue et al., "Electroporation as a New Technique for Producing Transgenic Fish," *Cell Differ. Dev.* 29(2):123–128 (1990).

Ishikawa et al., "Usefulness of the Medaka, *Oryzias latipes*, as a Test Animal: DNA Repair Processes in Medaka Exposed to Carcinogens," *Natl. Cancer Inst. Monograph* 65:35–43 (1984).

Ishikawa et al., "Importance of Hepatic Neoplasms in Lower Vertebrate Animals as a Tool in Cancer Research," *J. Toxicol. Environ. Health* 5:537–550 (1997).

Jakubczak et al., "Analysis of Genetic Instability During Mammary Tumor Progression Using a Novel Selection–based Assay for In Vivo Mutations in Bacteriophage Lambda Transgene Target," *Proc. Natl. Acad. Sci. USA* 93:9073–9078 (1996).

Kaiser, "Fishing for Toxic Chemicals," *Science* 283:775–777 (1999).

Kohler et al., "Spectra of Spontaneous and Mutagen–Induced Mutations in the lacI Gene in Transgenic Mice," *Proc. Natl. Acad. Sci. USA* 88:7958–7962 (1991).

Lebkowski et al., "The lacI Shuttle: Rapid Analysis of the Mutagenic Specificity of Ultraviolet Light in Human Cells," *Proc. Natl. Acad. Sci.* 82:8606–8610 (1985).

Lewis et al., "The Nature of Spontaneous and Induced Electrophoretically Detected Mutations in the Mouse," *Prog. Clin. Biol. Res.* 209B:359–365 (1986).

Lu et al., "Pantropic Retroviral Vector Integration, Expression, and Germline Transmission in Medaka (*Oryzias latipes*)," *Mol. Mar. Biol. Biotechnol.* 6(4):289–295 (1997).

Lu et al., "Integration, Expression, and Germ–line Transmission of Foreign Growth Hormone Genes in Medaka (*Oryzias latipes*)," *Mol. Marine Biol. and Biotechnol.* 1(4/5):366–375 (1992).

Masahito et al., "Fish Tumors and Their Importance in Cancer Research," *Jpn. J. Cancer Res.* 79:545–555 (1988).

Malling et al., "Use of $\phi$X174 as a Shuttle Vector for the Study of In Vivo Mammalian Mutagenesis," *Mutation Res.* 212:11–21 (1989).

Metcalfe, "Tests for Predicting Carcinogenicity in Fish," *CRC Rev. Aquat. Sci.* 1:111–129 (1989).

Mirsalis et al., "Induction of Hepatic Mutations in lacI Transgenic Mice," *Mutagenesis* 8:265–271 (1993).

Mirsalis et al., "Transgenic Animal Models for Detection of In Vivo Mutations," *Ann. Rev. Pharmacol. Toxicol.* 35:145–164 (1995).

Müller et al., "Introducing Foreign Genes into Fish Eggs with Electroporated Sperm as a Carrier," *Mol. Mar. Biol. Biotechnol.* 1 (4–5):276–281 (1992).

Müller et al., "Efficient Transient Expression System Based on Square Pulse Electroporation and In Vivo Luciferase Assay of Fertilized Fish Eggs," *FEBS Lett.* 324(1):27–32 (1993).

Murakami et al., "Micromachined Electroporation System for Transgenic Fish," *J. Biotechnol.* 34(1):35–42 (1994).

Nebert, "Transgenic Zebrafish–Sentinel for Aquatic Pollution", Abstract, Grant No. 5 R01 ES07058–02, 1 pg. (no later than Mar. 1998).

Ozato et al., "Production of Transgenic Fish: Introduction and Expression of Chicken $\delta$–crystallin Gene in Medaka Embryos," *Cell Differ.* 19:237–244 (1986).

Postlethwait et al., "Zebrafish Genomics: From Mutants to Genes," *Trends Genet.* 13(5):183–190 (1997).

Powers et al., "Electroporation: A Method for Transferring Genes into the Gametes of Zebrafish (*Brachydanio rerio*), Channel Catfish (*Ictalurus punctatus*), and Common Carp (*Cyprinus carpio*)," *Mol. Mar. Biol. Biotechnol.* 1(4–5):301–308 (1992).

Powers, "Fish as Model Systems," *Science* 246:352–358 (1989).

Provost et al., "Transgenic Systems for In Vivo Mutation Analysis," *Mutation Res.* 288:133–149 (1993).

Rogers et al., "Intralaboratory Optimization and Standardization of Mutant Screening Conditions Used for a Lambda/lacI Transgenic Mouse Mutagenesis Assay(I)," *Mutation Res.* 327:57–66 (1995).

Rokkones et al., "Microinjection and Expression of a Mouse Metallothionein Human Growth Hormone Fusion Gene in Fertilized Salmonid Eggs," *J. Comp. Physiol. B.*, 158:751–758 (1989).

Russell et al., "The Mouse Specific–Locus Test with Agents Other than Radiations, Interpretation of Data and Recommendations for Future Work," *Mutation Res.* 86:329–354 (1981).

Sambrook et al., "Preparation of Reagents and Buffers Used in Molecular Cloning," *Molecular Cloning* 2nd Ed., Cold Spring Harbor Press, p.B.13 (1989).

Schwarz et al., Nucleotide Sequence of cro, cII and Part of the o gene in phage $\lambda$ DNA *Nature* 272:410–414 (1978).

Shimada et al., "Some Characteristics of Radiation– or Enu–induced Mutations at the b Locus of the Medaka," *Phys. Gen.* 7(6):1053 (1990).

Shimada et al., "Further Characterization of Radiation– or Enu–induced Mutations at the b Locus of the Medaka," *Genetics* 8(6):1127 (1991).

Singer, "All Oxygens in Nucleic Acids React with Carcinogenic Ethylating Agents," *Nature* 264:333–339 (1976).

Singer et al., "Oxygens in DNA are Main Targets for Ethylnitrosourea in Normal and *Xeroderma Pigmentosum* Fibroblasts and Fetal Rat Brain Cells," *Nature* 276:85–88 (1978).

Skopek et al., "Relative Sensitivity of the Endogenous hprt Gene and lacI Transgene in ENU–Treated Big Blue™ B6C3F1 Mice," *Environ. Mol. Mut.* 26(1):9–15 (1995).

Streisinger et al., "Production of Clones of Homozygous Diploid Zebra Fish (*Brachydanio rerio*), " *Nature* 291:293–296 (1981).

Symonds et al., "Development of a Mass Gene Transfer Method in Chinook Salmon: Optimization of Gene Transfer by Electroplated Sperm," *Mol. Mar. Biol. Biotechnol.* 3(2):104–111 (1994).

Szelei et al., "Entrapment of High–Molecular–Mass DNA Molecules in Liposomes for the Genetic Transformation of Animal Cells," *Biochem. J.* 259:549–553 (1989).

Tamiya et al., "Spatial Imaging of Luciferase Gene Expression in Transgenic Fish," *Nucleic Acids Res.* 18:1072 (1990).

Tennant et al., "Prediction of Chemical Carcinogenicity in Rodent from In Vitro Genetic Toxicity Assays," *Science* 236:933–941 (1987).

Tsai et al., "Initiation of the Transgenic lacZ Gene Expression in Medaka (*Oryzias latipes*) Embryos," *Mol. Mar. Biotechnol.* 4(1):1–9 (1995).

Valcovic et al., "An Approach to Measuring Germinal Mutations in the Mouse," *Environ. Health Perspect.* 6:201–205 (1973).

Van Beneden et al., "Oncogenes in Hematopoietic and Hepatic Fish Neoplasms," *Cancer Res.* 50:5671s–5674s (1990).

Vogelstein et al., "Genetic Alterations During Colorectal–Tumor Development," *N. Eng. J. Med.* 319(9):525–532 (1988).

Walker et al., "A Small Fish Model for Assessing Cancer Risk at Low Carcinogen Concentrations," *Toxicologist* 12, Abstract No. 302 (1992).

Winn et al., "Transfer, Methylation and Spontaneous Mutation Frequency of φX174am3cs70 sequences in Medaka (*Oryzias latipes*) and Mummichog (*Fundulus heteroclitus*): Implications for Gene Transfer and Environmental Mutagenesis in Aquatic Species," *Marine Environ. Res.* 40(3):247–265 (1995).

Winn, "Transgenic Fish Model for Mutation Detection", Abstract, Grant No. 1 R24 RR11733–01A1, 1 pg., (no later than Mar. 1998).

Yamamoto, "Medaka (Killifish): Biology and Strains," Keigaku Publishing Co., Toyko, Japan, Title Page and Table of Contents (1975).

Zelenin et al., "The Delivery of Foreign Genes into Fertilized Fish Eggs Using High–Velocity Microprojectiles," *FEBS Lett.* 287(1–2):118–120 (1991).

International Agency for Research on Cancer (IARC), IARC Monographs on the Evaluation of the Carcinogenic Risk of Chemicals to Humans, 7, IARC, Lyon., 253–260 (1974).

"λ Select–cII™ Mutation Detection System for the Big Blue® Rodents," Instruction Manual, Stratagene, Catalog #720120, Revision #028001, p. 1–21 (1998).

"cII Primers Product" Information Sheets, Epicentre Technologies, Catalog #P67PL1, and #P67PL2, 1 pg. (1996).

Big Blue™ Transgenic Mouse Mutagenesis Assay System, Instruction Manual Title Page and Table of Contents, 2 pgs. (Aug. 1992).

http://www.stratagene.com/vol10_3/figures/p100–101.htm, "Big Blue™ γLIZ Shuttle Vector", 1 pg. (May 1998).

http://www.stratagene.com/vol10_3/figures/p100–101–fl.htm, "A Positive Selection Assay for Mutation Analysis in Big Blue™ Animals", 2 pgs. (May 1998).

http://www.stratagene.com/tech_ref/big_blue/faq.htm, "Technical Information—Stratagene Online", 3 pgs. (Mar. 1998).

http://darwin.ceh.uvic.ca/bigblue/bbinfo.htm, "A short description of the Big Blue system", 1 pg. (May 1998).

http://darwin.ceh.uvic.ca/bigblue/cci–info.htm, "A short description of the lambda cII system", 1 pg. (May 1998).

http://www.interscience.com/epicentre/mutplxc2.html, "MutaPlax™ Transgenic Lambda DNA Packaging System", 1 pg. (May 1998).

http://www.interscience.com/epicentre/mutplxc2.html, "MutaPlax cII–Select™ Packaging and Selection Kit", 1 pg. (May 1998).

* cited by examiner

A

| λ bp | nt | (↑ cI ORF ends at λ base position 37230) |
|---|---|---|
| | | SEQ ID NO:1 |
| 37814 | | TCC CCA TCT TGT CTG CGA CAG ATT CCT GGG ATA AGC CAA GTT CAT TTT TCT TTT |
| 37868 | | TTT CAT AAA TTG CTT TAA GGC GAC GTG CGT CCT CAA GCT GCT CTT GTG TTA ATG |
| | | cI start ←\|      $O_{R3}$ |
| 37922 | | GTT TCT TTT TTG TGC TCA Tac gtt aaa tct atc acc gca agg gat aaa tat cta |
| | | $O_{R2}$      $O_{R1}$  $P_R$ promoter 5' mRNA → |
| 37976 | | aca ccg tgc gtg ttg act att tta cct ctg gcg gtg ata atg gtt gca tgt act |
| | | \|→ start Cro |
| 38030 | 8 | aag gag gtt gtA TGG AAC AAC GCA TAA CCC TGA AAG ATT ATG CAA TGC GCT TTG |
| 38084 | 62 | GGC AAA CCA AGA CAG CTA AAG ATC TCG GCG TAT ATC AAA GCG CGA TCA ACA AGG |
| 38138 | 116 | CCA TTC ATG CAG GCC GAA AGA TTT TTT TAA CTA TAA ACG CTG ATG GAA GCG TTT |
| | | end Cro →\| |
| 38192 | 170 | ATG CGG AAG AGG TAA AGC CCT TCC CGA GTA ACA AAA AAA CAA CAG CAT AAa taa |
| | | [Alternative sequencing primer→]       [PCR &] |
| 38246 | 224 | ccc cgc tct tac aca ttc cag ccc tga aaa agg gca tca aat taa acc aca cct |
| | | [sequencing primer→]                SD |
| 38300 | | atg gtg tat gca ttt att tgc ata cat tca atc aat tgt tat cta agg gaa tac |
| | | \|→ start cII                367 |
| 38354 | 332 | tta cat ATG GTT CGT GCA AAC AAA CGC AAC GAG GCT CTA CGA ATC GAG AGT GCG |
| | SEQ ID NO:2 | Met Val Arg Ala Asn Lys Arg Asn Glu Ala Leu Arg Ile Glu Ser Ala |
| | | 403                     421 |
| 38408 | 386 | TTG CTT AAC AAA ATC GCA ATG CTT GGA ACT GAG AAG ACA GCG GAA GCT GTG GGC |
| | | Leu Leu Asn Lys Ile Ala Met Leu Gly Thr Glu Lys Thr Ala Glu Ala Val Gly |
| | | 457              475 |
| 38462 | 440 | GTT GAT AAG TCG CAG ATC AGC AGG TGG AAG AGG GAC TGG ATT CCA AAG TTC TCA |
| | | Val Asp Lys Ser Gln Ile Ser Arg Trp Lys Arg Asp Trp Ile Pro Lys Phe Ser |
| | | 511             529 |
| 38516 | 494 | ATG CTG CTT GCT GTT CTT GAA TGG GGG GTC GTT GAC GAC GAC ATG GCT CGA TTG |
| | | Met Leu Leu Ala Val Leu Glu Trp Gly Val Val Asp Asp Asp Met Ala Arg Leu |
| | | 565             583 |
| 38570 | 548 | GCG CGA CAA GTT GCT GCG ATT CTC ACC AAT AAA AAA CGC CCG GCG GCA ACC GAG |
| | | Ala Arg Gln Val Ala Ala Ile Leu Thr Asn Lys Lys Arg Pro Ala Ala Thr Glu |
| | | 619    end cII →\| |
| 38624 | 602 | CGT TCT GAA CAA ATC CAG ATG GAG TTC TGA ggt cat tac tgg atc tat caa cag |
| | | Arg Ser Glu Gln Ile Gln Met Glu Phe --- |
| | | \|→ start O      [← PCR & sequencing primer] |
| 38678 | 656 | gag tca ttA TGA CAA ATA CAG CAA AAA TAC TCA ACT TCG GCA GAG GTA ACT TTG |

SEQ ID NO:3   cII Primer 1
───────────────────────▶
AAAAAGGGCATCAAATTAAACCACACCTATGGTGTATGCATTTATTTGCATACATTCAATCAATTGTT
ATCTAAGGAAATACTTACAT<u>ATG</u>GTTCGTGCAAACAAACGCAACGAGGCTCTACGAATCGAGAGTGC
GTTGCTTAACAAAATCGCAATGCTTGGAACTGAGAAGACAGCGGAAGCTGTGGGCGTTGATAAGTC
GCAGATCAGCAGGTGGAAGAGGGACTGGATTCCAAAGTTCTCAATGCTGCTTGCTGTTCTTGAATG
GGGGGTCGTTGACGACGACATGGCTCGATTGGCGCGACAAGTTGCTGCGATTCTCACCAATAAAAA
ACGCCCGGCGGCAACCGAGCGTTCTGAACAAATCCAGATGGGAGTTC<u>TGA</u>GGTCATTACTGGATCTA
TCAACAGGAGTCATTATGACAAATACAGCAAAAATACTCAACTTCGG
                              ◀───────────────────────
                                      cII Primer 2

Fig. 2 (continued)

BACTERIOPHAGE-BASED TRANSGENIC FISH FOR MUTATION DETECTION

This application claims the benefit of U.S. Provisional Application No. 60,087,430, filed May 31, 1998.

STATEMENT OF GOVERNMENT RIGHTS

This invention was made with government support under a grant from the National Institutes of Health, Grant No. RR11733-01. The U.S. Government has certain rights in this invention.

FIELD OF THE INVENTION

This invention relates to a transgenic fish carrying a bacteriophage-derived transgene construct, and in particular relates to a transgenic fish for use in evaluating the effect of a potential mutagenic agent or event. The transgenic fish is exposed to the mutagenic agent or event, and mutagenesis is detected by assaying for a mutation target nucleic acid sequence present as a genomically integrated transgene in the transgenic fish.

BACKGROUND OF THE INVENTION

Thousands of chemicals are currently in commercial use in the USA, some of which pose significant health risk to humans. Among these toxicants are mutagens to which exposure is likely to cause genetic changes that lead to somatic or inherited diseases. In particular, cancer has been shown to result from a series of mutations in specific oncogenes and tumor suppressor genes (B. Vogelstein et al., *N. Engl. J. Med.* 319: 525–532 (1988)). Despite the recognition of the role of chemically-induced mutation as an important event leading to disease, few methods are available for the assessment of genetic hazard, or focus on the study of gene mutations as they occur at the DNA level in vivo. As a result, there is an immediate need to develop sensitive and biologically relevant methods that can be applied to the study of the mechanisms of mutagenesis and hazard assessment.

Until recently, progress in the analysis of gene mutations directly at the DNA level was limited by the standard molecular techniques and the available endogenous genes. During past years, the most relevant assays for induction of transmissible mutations have been based on the appearance of visible or biochemical mutations among the offspring of exposed mice (L. B. Russell et al., *Mutation Res.* 86: 329–354 (1981); L. R. Valcovic et al., *Environ. Health Perspect.* 6:201–205 (1973); S. E. Lewis et al., *Prog. Clin. Biol. Res.* 209B. 359–365 1986)). These tests cannot be practically applied to large numbers of compounds because they require extensive resources and very large numbers of animals. The tests also fail to provide information regarding somatic mutagenesis or clustering of mutations, which may be important in the understanding of the development of various diseases.

In order to circumvent some of the problems inherent in rodent assays, short-term mutagenicity tests were developed, based on the assumption that many of the chemicals toxic to rodents would also be genotoxic to bacteria. However, an analysis by the National Toxicology Program (R. W. Tennant et al., *Science* 236:933–941 1987)) revealed significant differences in results between rodent and bacterial tests. This failure of predictive correlation may be related to: 1) a lack of understanding of the roles mutation plays in cell transformation, and 2) differences between animals and bacterial cells in terms of exposure, biological milieu, metabolism, replication and repair. While comparisons between animals and animal cells in culture provide appropriate genomic similarity, there are few known biological markers for mutation of cells in culture. The biological markers that have been identified are restricted to specific cell types and therefore are of limited use for in vivo comparisons.

There thus remains a need to combine the simplicity of short-term in vitro assays with in vivo studies. Ultimately, reliable and realistic hazard assessment and informative mechanistic studies of mutagenesis require the development of practical methods for evaluating somatic and genetic events in whole animals exposed to environmental agents. New approaches that use recombinant DNA and gene transfer techniques to develop transgenic animal models offer significant promise for in vivo studies of mutagenesis, cancer, birth defects and other diseases (T. L. Goldsworthy et al., *Fund. Appl. Toxicol.* 22:8–19 (1994)). To be effective, the transgenic approach as applied to mutagenesis should include the following components: 1) unique genes with known sequences; 2) a capacity to observe changes at the single copy level; 3) an easily attainable sample population of sufficient size to allow measurement of low frequency events; and 4) the ability to determine the exact nature of the mutation, independent of the host phenotype.

Transgenic animal models have been developed. Typically, transgenic animals are produced by the transfer of novel DNA sequences into the animal's genome followed by transmission of the sequence to subsequent generations. The use of transgenic rodents that carry genes specifically designed for the quantitation of spontaneous and induced mutations is a major advancement in rapidly analyzing tissue-specific mutations in a whole organism following mutagenic agent exposure (J. C. Mirsalis et al., *Ann. Rev. Pharmacol. Toxicol.* 35:145–164 1995)).

Mutagenesis assay systems that utilize transgenic animals typically rely on bacteriophage or plasmid shuttle vectors to carry the mutation target. The basic principle in this approach is that a recombinant gene carrying a mutation target is introduced into the genome of a host animal using the shuttle vector. Following exposure to a mutagen, the target gene is recovered from the transgenic animal and serves as an indicator of mutagenesis (reviewed by R. B. Dubridge et al., *Mutagenesis* 3(1):1–9 (1988)). Two forms of bacteriophage shuttle vectors are most commonly in use. One is known as the $\psi$X174 integrated shuttle vector. This vector is recovered from the transgenic host, transfected into a suitable *E. coli* host, and mutations at specific locations in the phage sequence are identified by suppressor-mediated selection on permissive and non-permissive *E. coli* (H. V. Malling et al., *Mutation Res.* 212:11–21 (1989); R. N. Winn et al., *Marine Environ. Res.* 40(3):247–265 (1995)).

Another useful mutagenesis detection system is based on a lambda ($\lambda$) phage-based recombinant vector which combines cos site packaging for recovery of the phage sequence from the host DNA with the use of the lacI or lacZ target gene for mutation detection (J. S. Lebkowski et al., *Proc. Natl. Acad. Sci.* 82:8606–8610 (1985); J. A. Gossen et al., *Proc. Natl. Acad. Sci.* 86:7971–7975 (1989)).

Mutation-induced inactivation of the lac genes is detected after recovery of the shuttle sequence from the transgenic host, typically via complementation assay in *E. coli*. See U.S. Pat. No. 5,589,155 (Sorge et al., Dec. 31, 1996); U.S. Pat. No. 5,347,075 (Sorge, Sep. 13, 1994); and U.S. Pat. No. 5,510,099 (Short et al., Apr. 23, 1996), the texts of which are incorporated by reference, in their entireties, as if fully set forth herein. A mutation detection system based on the lacI gene as the mutation target, known by the tradename BIG BLUE, is commercially available from Stratagene Inc. (La Jolla, Calif.). The vector used in BIG BLUE mutagenesis detection system is known as λLIZ, and the genetic map of this vector is shown in FIG. 1.

The λLIZ vector contains an additional mutagenesis target in the form of the cII region (see FIG. 1). Mutations in the cII gene and at certain related locations in the cII region can be detected by evaluating whether an *E. coli* host that has been infected with the shuttle sequence recovered from the transgenic host can multiply through the lytic or the lysogenic cycle (J. L. Jakubczak et al., *Proc. Natl. Acad. Sci. U.S.A.*, 93:9073–9078 (1996)). The commitment to either lysis or lysogeny made by lambda phage upon infection of an *E. coli* cell is regulated by a group of proteins, one of which is the product of the cII gene. Mutagenesis detection packaging and selection systems based upon the cII region as the mutation target sequence are commercially available from Stratagene Inc., La Jolla, Calif. (available under tradename λ SELECT-cII) and Epicentre Technologies, Madison, Wis. (available under the tradename MutaPlax cII-Select Packaging and Selection Kit).

To date, the lambda (λ) phage-based recombinant vectors disclosed in U.S. Pat. Nos. 5,589,155, 5,347,075, and 5,510,099; European Patent No. 0289121; and Japanese Patent No. 2618973, each of which is incorporated herein in its entirety, have been used successfully for detection of mutagenic events only in selected mammalian cell lines, mice and rats. Alternative animal models are thus much needed. Fish as transgenic hosts are especially desirable because they are environmentally relevant models for health risk assessment of aquatic and marine systems. There is also increasing appreciation of their suitability for biomedical applications. The fish is an alternative, nonmammalian animal model that can be used to refine, reduce or replace traditional animal models used in research and testing.

SUMMARY OF THE INVENTION

The present invention provides a transgenic fish containing a genomically integrated bacteriophage lambda-derived transgene construct. The invention further includes a transgenic fish gamete, including a transgenic fish egg or sperm cell, a transgenic fish embryo, or other transgenic fish cell or cluster of cells, whether haploid, diploid, triploid, or other zygosity, which contain a genomically integrated bacteriophage lambda-derived transgene construct. A transgene construct that is "bacteriophage lambda-derived" is a construct that is based on the bacteriophage lambda. Preferably, the bacteriophage lambda-derived transgene construct is genomically integrated into the fish's somatic and germ cells such that it is stable and inheritable. Progeny of a transgenic fish containing a genomically integrated bacteriophage lambda-derived transgene construct, and transgenic fish derived from a transgenic fish egg, sperm cell, embryo, or other cell containing a genomically integrated bacteriophage lambda-derived transgene construct, are also included in the invention. A fish is "derived from" a transgenic fish egg, sperm cell, embryo or other cell if the transgenic fish egg, sperm cell, embryo or other cell contributes DNA to the fish's genomic DNA. For example, a transgenic embryo of the invention can develop into a transgenic fish of the invention; a transgenic egg of the invention can be fertilized to create a transgenic embryo of the invention that develops into a transgenic fish of the invention; a transgenic sperm cell of the invention can be used to fertilize an egg to create a transgenic embryo of the invention that develops into a transgenic fish of the invention; and a transgenic cell of the invention can be used to clone a transgenic fish of the invention. In some preferred embodiments of the invention, the transgenic fish is sterile.

The transgenic fish of the invention is preferably a teleost (boney) fish, but also includes a cartilagenous fish. Conveniently, the transgenic fish can be selected from among the well-known group of laboratory model fish which include medaka, zebrafish, mummichog, killifish, channel catfish, common carp and trout. In a particularly preferred embodiment, the transgenic fish is a medaka.

Further, the present invention includes a cell line derived from a transgenic fish embryo or other transgenic fish cell of the invention, which contains a genomically integrated bacteriophage lambda-derived transgene construct.

The bacteriophage lambda-derived transgene construct preferably comprises an excisable test nucleic acid sequence that contains at least one copy of an assayable mutation target nucleic acid sequence. The assayable mutation target nucleic acid sequence is heterologous with respect to the fish genome. Two or more different assayable mutation target nucleic acid sequences can optionally be present in the bacteriophage lambda-derived transgene construct. In a particularly preferred embodiment, a mutation in the assayable mutation target nucleic acid sequence is detectable via bioassay in a bacterial cell, such as an *E. coli* cell, into which the assayable mutation target nucleic acid sequence has been introduced. In this regard, a transgenic fish of the invention that has a triploid genome is especially preferred because the larger amount of DNA in triploid genomes increases the efficiency of DNA recovery. An increase in the amount of DNA recovered has many advantages. For example, it allows for more efficient detection of the mutation target nucleic acid. Moreover, fish having a triploid genome are typically sterile, which may be desirable for certain applications or studies.

The assayable mutation target nucleic acid sequence preferably contains at least one nucleic acid sequence selected from the group consisting of the lacI gene, the lacZ gene, the lac promoter sequence, the cII gene, the cII mRNA ribosome binding site, and the cII protein-activated $P_{RE}$ promoter.

The invention further includes a genomically identical population of transgenic fish, each of whose somatic and germ cells contain a genomically integrated bacteriophage lambda-derived transgene construct. The genomically identical population is a unisex population and can be male or female. Preferably, the genomically integrated bacteriophage lambda-derived transgene construct present in the genomically identical population contains an excisable test nucleic acid sequence comprising at least one copy of one or more assayable mutation target nucleic acid sequences. Preferred embodiments of the genomically identical transgenic fish population are essentially as described for the transgenic fish of the invention. In an alternative embodiment, the invention includes a population of transgenic fish, i.e., an in-bred line, the members of which are not necessarily genomically identical but are homozygous with respect to the bacteriophage lambda-derived transgene construct.

BRIEF DESCRIPTION OF THE DRAWINGS

FIGS. 2A and 2B depict (A) the nucleotide sequence (SEQ ID NO:1) of the lambda cII gene and the surrounding regions in the BIG BLUE λLIZ Shuttle Vector, as shown at page 15 in the Instruction Manual for the λ Select-cII Mutation Detection System for Big Blue Rodents (Catalog #7210210, Revision #028001, Stratagene, La Jolla, Calif.), and the amino acid sequence (SEQ ID NO:2) of the cII protein; and (B) the nucleotide sequence of the lambda cII gene (SEQ ID NO:3) and location of primer binding sites, taken from cII Primers Product Information Sheet (Cat. Nos. P67PL1, P67PL2, Epicentre Technologies, Madison, Wis.).

DETAILED DESCRIPTION OF THE INVENTION

Host Organism

Figure 1:
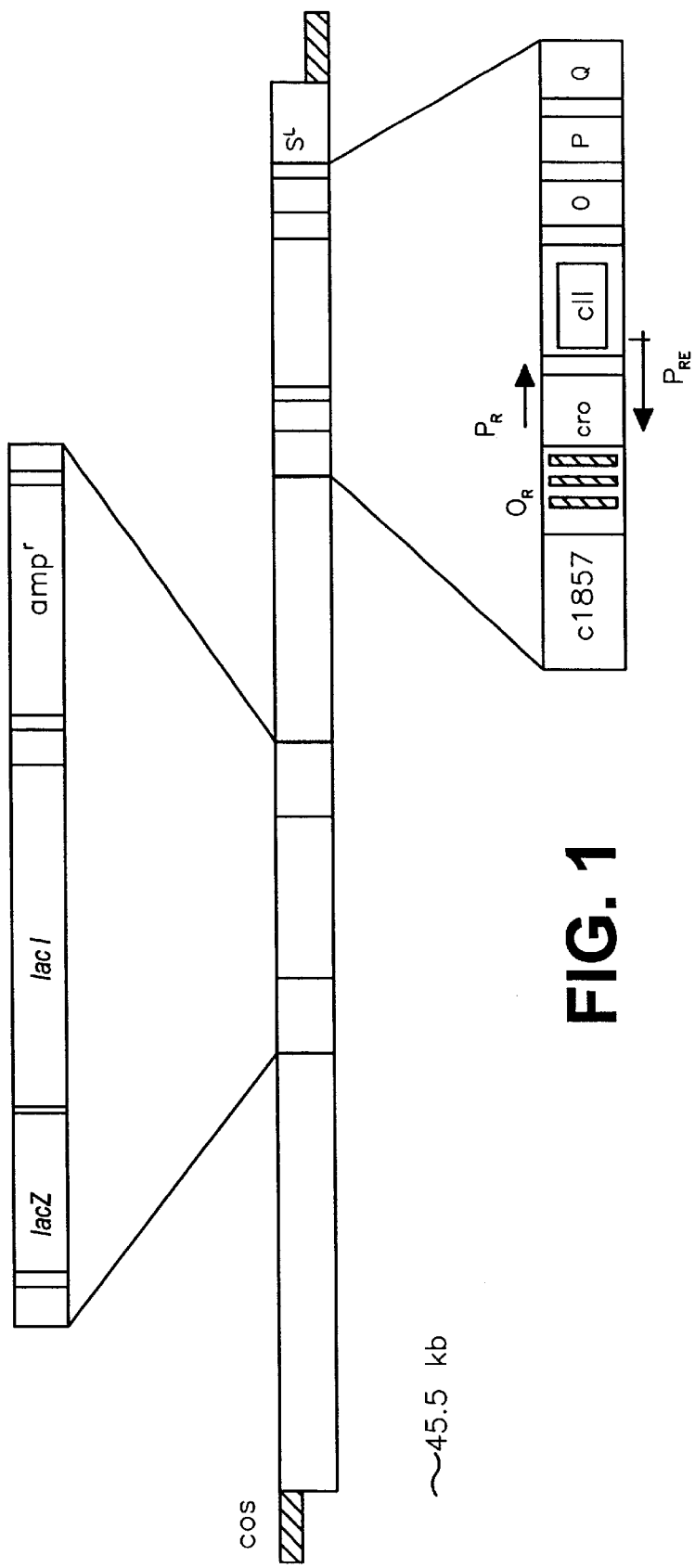
FIG. 1 is a schematic diagram of the BIG BLUE λLIZ shuttle vector (~45.5 kb) (Stratagene, Inc., La Jolla, Calif.); the expanded regions show (A) the area important for a plaque-color-screening assay to detect mutations, which contains lacI, and (B) the area important for a selection assay based upon mutation in the cII region.

There are many advantages to the use of fish to detect mutagenic agents or events. Fish are easily handled, manipulated, and observed without compromising natural development, and present opportunities for studies on multiple exposure routes via aqueous media. They exhibit excellent agent-specific responses to a variety of toxicants. Teleost fish, also known as the modern boney fishes, constitute the largest and most diverse division of vertebrates, with over 20,000 known species. Their diversity and phylogenetic positions make them ideal for comparative toxicological studies, which may allow more insight into basic mechanisms than would studies limited to mammalian models alone (D. A. Powers, *Science* 246:352–358 (1989)). Certain teleost fish, commonly referred to as laboratory aquarium fish or laboratory model species, have been extensively studied in research settings and are thus especially well-suited as transgenic hosts. Laboratory model species include, but are not limited to, medaka (*Oryzias latipes*), zebrafish (*Danio rerio*), mummichog (*Fundulus heteroclitus*), killifish (Fundulus spp.), channel catfish (*Ictalurus punctatus*), common carp (*Cyprinus carpio*) and trout. Cartilagenous fish such as sharks and rays, also known as chondrichthyes fish, are also suitable transgenic host organisms.

In addition to playing an important role in comparative mutagenesis studies, it is anticipated that the transgenic fish models may ultimately facilitate a broad range of exposure regimens such as long-term low-dose chronic exposures, controlled field-based in situ exposures or large-scale mesocosms, that were previously difficult or impossible to perform. Fish can be conveniently used for zygote-to-adult exposure studies, and offer flexibility in study designs related to numbers of exposure groups and exposure schedules.

Fish eggs are large, abundant, and often translucent, and can be fertilized in vitro. The resulting embryos are easily maintained and develop externally, obviating the need for reintroduction of the embryo into a receptive female. In addition, laboratory analyses can generally be performed more rapidly and at lower cost compared to rodent assays.

Heterologous genes have been introduced into fish beginning in 1985. Among these heterologous genes that have been introduced into fish include genes that code for growth hormones (human, rat, rainbow trout), chicken delta-crystalline protein, *E. coli* β-galactosidase, *E. coli* neomycin-resistance, and anti-freeze protein. However, numerous problems have been encountered in producing transgenic fish having stable, inheritable genomically integrated transgenes. For example, mosaicism is a common problem in the creation of transgenic fish. Mosaic organisms do not contain the transgene in every somatic and germ cell, and thus may not be capable of producing transgenic offspring. Mosiacism arises from fact that microinjection of heterologous DNA into a fish embryo often delivers the heterologous DNA to the cytoplasm rather than the cell nucleus.

Despite the evolutionary distance between fish and humans, there is increasing evidence for correlation between environmentally-induced fish and human diseases. Fish can be exposed to different concentrations of known or suspected toxicants and can provide fundamental information related to substance toxicity and carcinogenicity/mutagenicity. The use of fish in carcinogenesis research, in particular, has received considerable attention related to the potential of fish for identifying and predicting human health effects (W. F. Hawkins et al., Chapter 14 in G. M. Rand, ed., Fundamentals of Aquatic Toxicology: Effects, Environmental Fate, and Risk Assessment, Taylor and Francis. 421–446 (1995); J. D. Hendricks, In L. J. Weber, ed., Aquatic Toxicology, Raven Press, New York. 149–211 (1982); J. J. Black, In J. Saxena, ed., Hazard Assessment of Chemicals: Current Developments, Vol. 3. Academic Press, New York. 181–232 (1984); C. D. Metcalfe, *CRC Rev. Aquat. Sci.* 1:111–129 (1989)). The fact that many fish species appear to be sensitive to the carcinogenic effects of certain chemicals while having low spontaneous rates of neoplasia supports the use of fish in various assays as alternatives or supplements to rodent chronic bioassays (G. D. Bailey et al., *Environ. Health Perspect.* 71:147–153 (1987); T. Ishikawa et al., *J. Toxicol. Environ. Health* 5:537–550 (1977); P. Masahito et al., *Jpn. J Cancer Res.* 79:545–555 (1988)).

The genetics, developmental biology and embryology of medaka (*Oryzias latipes*) are well-documented, and specific developmental stages have been extensively characterized (T. O. Yamamoto, Medaka (killifish): Biology and Strains. Keigaku Publishing Co., Tokyo, Japan. (1975)). Medaka is typically used to study aspects of various diseases in which large numbers of experimental organisms are required, such as in low-dose risk assessment, as well as to examine factors that only slightly increase hazard exposure risk (W. W. Walker, W. E. Hawkins, R. M. Overstreet, and M. A. Friedman, "A small fish model for assessing cancer risk at low carcinogen concentrations," *Toxicologist* 302 (1992)). The use of medaka in biomedical research, especially as a carcinogenesis model related to the potential for identifying and predicting human effects from toxicant exposure, has received considerable attention in recent years (W. E. Hawkins et al., Chapter 14 in G. M. Rand, ed., Fundamentals of Aquatic Toxicology: Effects, Environmental Fate, and Risk Assessment, Taylor and Francis. 421–446 (1995); J. D. Hendricks, In L. J. Weber, ed., Aquatic Toxicology, Raven Press, New York. 149–211 (1982); J. J. Black, In J. Saxena, ed., Hazard Assessment of Chemicals: Current Developments, Vol. 3. Academic Press, New York. 181–232 (1984); and C. D. Metcalfe, *CRC Rev. Aquat. Sci.* 1:111–129 (1989)). The sensitivity of medaka to many carcinogens, the availability of specimens, and the degree of control that can be maintained over extraneous factors all contribute to this small fish being one of the most widely used species for studies in comparative toxicology (W. E. Hawkins et al., Chapter 14 in G. M. Rand, ed., Fundamentals of Aquatic Toxicology: Effects, Environmental Fate, and Risk Assessment, Taylor and Francis. 421–446 (1995)), the biology of hepatic neoplasia (D. E. Hinton et al., *Aquat. Toxicol.* 11:77–112 (1988)), oncogene activation (R. J. Van Beneden et al., *Cancer Res.* 50:5671s–5674s (1990)), DNA repair (T. Ishikawa et al., *Natl. Cancer Inst. Monograph* 65:35–43 (1984)), and mutagenesis (R. N. Winn et al., *Marine Environ. Res.* 40(3):247–265 (1995)).

Medaka offer numerous advantages for transgenic development such as small size (about 2.5 cm), relatively short generation time (1–2 months), and prolific capacity to reproduce (more than 3,000 eggs/female in a single breeding season). Spawning can be induced year-round by maintaining breeding stocks at 25–28° C. and eggs usually hatch in 10 days at 25° C. Eggs are translucent, which greatly facilitates the positioning of fine glass needles for DNA microinjection. Medaka was the first transgenic fish species produced to demonstrate successful foreign gene expression (K. Ozato et al., *Cell Differ.* 19:237–244 (1986)). Subsequently, numerous transgenic medaka have been produced that carry a variety of transgenes (e.g. K. Inoue et al., *Cell Differ. Dev.* 27(1):57–68 (1989); E. Tamiya et al., *Nucleic Acids Res.* 18:1072 (1990); K. Inoue et al., *Cell Differ. Dev.* 29(2):123–128 (1990); J. Lu et al., *Mol. Marine Biol. and Biotechnol.* 1(4/5):366–375 (1992); H. J. Tsu et al., *Mol. Mar. Biol. Biotechnol.* 4(1):1–9 (1995); R. N. Winn et al., *Marine Env. Res.* 40(3):247–265 (1995)).

As noted above, the invention is intended to further encompass progeny of a transgenic fish containing a genomically integrated bacteriophage lambda-derived transgene construct, as well as transgenic fish derived from a transgenic fish egg, sperm cell, embryo, or other cell containing a genomically integrated bacteriophage lambda-derived transgene construct. "Progeny", as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The hybrid progeny of these matings have the benefits of the transgene for mutation detection combined with the benefits derived from these other lineages.

Definitions

An "expression vector" is a nucleic acid molecule containing a nucleotide sequence that is expressed in a host cell. Typically, the expression vector is a DNA molecule containing a gene, and expression of the gene is under the control of regulatory elements that can, but need not, include one or more constitutive or inducible promoters, tissue-specific regulatory elements, and enhancers. Such a gene or nucleic acid sequence is said to be "operably linked to" the regulatory elements.

A "cloning vector" is a nucleic acid molecule, typically a DNA molecule, that has the capability of replicating autonomously in a host cell. The cloning vector can, for example, be a plasmid, cosmid, or bacteriophage, and can be linear or circular. Cloning vectors typically contain one or more restriction endonuclease recognition sites at which foreign nucleic acid sequences can be inserted in a determinable fashion without loss of an essential biological function of the vector, as well as a marker sequence that is suitable for use in the identification and selection of cells transformed with the cloning vector. Marker genes typically include nucleic acid sequences that encode polypeptides which can confer a phenotypic characteristic to the transformed cell, such as antibiotic resistance, test compound metabolism, and the like.

The terms "exogenous" or "heterologous," which are used interchangeably herein, denote some item, typically a nucleic acid sequence, that is foreign to its surroundings. In particular, the terms apply to nucleic acid sequences that have been inserted in to a host organism, but are not found in the normal genetic complement (i.e., genome) of the host organism. A gene that is heterologous with respect to an organism into which it has been inserted or transferred is sometimes referred to herein as a "transgene." A "transgenic" animal or host is an animal having one or more cells that contain exogenous (heterologous) nucleic acid sequences, including expression vectors. Although introduction of the heterologous nucleic acids into a host cell is not limited to any particular mode of delivery, microinjection of the heterologous DNA is preferred. Microinjection is labor-intensive and time-consuming, but when practiced in accordance with the present invention results in a greater likelihood of introducing the DNA into the cell nucleus as opposed to the cytoplasm. While advances have been made relating to other methods of gene transfer such as electroporation of eggs (e.g., K. Inoue et al., *Cell Differ. Dev.* 29(2):123–128 (1990); F. Muller et al., *FEBS Lett.,* 324 (1):27–32 (1993); Y. Murakami et al., *J. Biotechnol.,* 34 (1):35–42 (1994); F. Muller et al., *Mol. Mar. Biol. Biotechnol.* 1 (4–5):276–81 (1992)) and sperm (Symonds et al., 1994; D. A. Powers et al., *Mol. Mar. Biol. Biotechnol.,* 1 (4–5):301–8 (1992)); particle gun bombardment (A. V. Zelenin et al., *FEBS Lett.,* 287 (1–2):118–20 (1991); liposomes (J. Szelei et al., *Biochem. J.,* 259 (2):549–53 (1989); and retroviral vectors (J. K. Lu et al., *Mol. Mar. Bio. Biotechnol.,* 6 (4):289–95 (1997)); these procedures only rarely result in transgene integration and germline transmission (K. Inoue et al., *Cell Differ. Dev.* 29(2):123–128 (1990)). Nonetheless, the invention is not intended to be limited to any particular method of introducing the heterologous DNA into the host organism. Preferably, the heterologous nucleic acid sequences are stably integrated into the host genome and are inheritable.

A "genomically identical" population of transgenic fish is one wherein each fish has the same genomic DNA as the others in the population; this can also be referred to as a clonal population. Members of a genomically identical population are produced by cloning or inbreeding within the population rather than by mating with non-genomically identical fish (see, e.g., D. C. Streisinger et al., *Nature,* 291:293–296 (1981); W. Driever et al., *Trends Genet.,* 10 (5): 152–159 (1994)). Zygosity of the genomically identical population can be haploid, diploid or triploid. A genomically identical population is a single sex (unisex) population and can be male or female. A genomically identical female population can be produced, for example, by gynogenesis, wherein sperm is used to activate the egg but does not contribute genomic DNA to the developing organism (J. H. Postlethwait et al., *Trends Genet.,* 13(5):183–190 (1997)). Methods for making a genomically identical male population include heat shock or irradiation.

A nucleotide sequence that is "excisable" from genomic DNA is one that can be isolated from the genomic DNA of the host animal, as by cutting the nucleotide sequence at one or more predetermined sites, for example at a lambda bacteriophage cos site. An "assayable" mutation target nucleic acid sequence is one wherein a mutated form of the nucleic acid sequence can be distinguished from the non-mutated form of the nucleic acid sequence, either directly or indirectly, as by using a laboratory assay or other detection procedure. Preferably, the presence or absence of a mutation in the nucleic acid sequence is detectable by way of a chemical or biological assay. Detection can be mediated through the use of "reporter" nucleic acid sequences. For example, in a lac operon-based mutation detection system, a mutation in a lacI mutation target gene affects the expression of the lacZ reporter gene, and expression of the reporter gene is detectable in an *E. coli* host by assaying the ability of the host to produce the lacZ gene product (β-galactosidase) and thus metabolize a chromogenic substrate.

The term "mutagen" is to be broadly understood as meaning any mutagenic or potentially mutagenic agent or event, including a mutagenic chemical compound, such as a toxicant, or exposure to radiation, including but not limited to alpha, beta, or gamma emissions from an radioisotope, electromagnetic radiation of any frequency, such as x-ray, ultraviolet, or infrared radiation, exposure to an electromagnetic field (EMF), and the like.

Mutation Target Nucleic Acid Sequences

The assayable mutation target nucleic acid sequences present in the preferred transgenic fish of the invention are conveniently included in a bacteriophage λ shuttle vector. Use of a shuttle vector facilitates both introduction of DNA into the fish and recovery or rescue of the DNA from the fish. The shuttle vector preferably includes an excisable test nucleic acid sequence that contains at least one copy of at least one assayable mutation target nucleic acid sequence. The shuttle vector may, however, contain multiple copies of a particular target sequence, and/or two or more different assayable mutation target nucleic acid sequences.

In one preferred embodiment, the assayable mutation target nucleic acid sequence comprises at least one nucleotide sequence selected from the nucleotide sequences of the lac operon. Preferably, the assayable mutation target nucleic acid sequence is at least one of the lacI gene, the lacZ gene, or the lac promoter sequence. More preferably, the assayable mutation target nucleic acid sequence is the lacI gene.

In another preferred embodiment, the assayable mutation target nucleic acid sequence comprises at least one nucleotide sequence selected from the nucleotide sequences of the cII region of bacteriophage lambda. The cII region of bacteriophage lambda is approximately 300 base pairs in length and encompasses, among other sequences, the $P_R$ promoter, the cII gene (which encodes the cII protein), the cII gene (which encodes the cII repressor protein), the cII MRNA ribosome binding site, and the cII protein-activated PRE promoter. Preferably, the assayable mutation target nucleic acid sequence is at least one of the cII gene, the cII mRNA ribosome binding site gene, or the $P_{RE}$ promoter sequence. More preferably, the assayable mutation target nucleic acid sequence is the cII gene.

The nucleotide sequence of the bacteriophage lambda cII region, as disclosed in the Instruction Manual for the λ Select-cII Mutation Detection System for Big Blue Rodents (Catalog #7210210, Revision #028001, incorporated herein in its entirety) is set forth in FIG. 2A. The λ base positions (λ bp) displayed in the far left column are derived from the base positions of the wild-type lambda sequence (GenBank database accession numbers J02459, M17233, M24325, V00636 and X00906). The numbering convention used for the cII nucleotide positions (nt) listed in the second column is that of Schwarz et al. (*Nature,* 272: 410–414 (1978)). The positions of the cII PCR and sequencing primers used in the Stratagene mutation detection system are labeled. The cII primers used for PCR or sequencing of the cII gene in the alternative Epicentre Technologies mutation detection system are shown in FIG. 2B.

The cII protein activates transcriptional promoters in lambda that are essential for lysogenization in a bacterial host. Mutations in the cII region that lower the levels of cII protein result in a decreased ability of lambda to lysogenize. When grown under conditions that favor lysogeny in a suitable bacterial host cell, preferably an hfl⁻ *E. coli* strain, lambda prophages carrying such mutations survive only by the entering the lytic pathway of development, forming plaques. Prophages that are wild type for the cII region integrate into the bacterial host genome and become part of the developing bacterial lawn.

In a particularly preferred embodiment of the invention, the shuttle vector used to transfect the host fish cell is BIG BLUE λLIZ shuttle vector. This shuttle vector contains at least two mutation target regions: one derived from the lac operon, and the other comprising the lambda cII region. The packaging extract provided by Stratagene, Inc., recognizes the cos sites of the integrated lambda DNA and packages the sequences between the cos sites into phage particles. After the shuttle vector is recovered from the fish, the vector is packaged and introduced into an appropriate bacterial host *E. coli,* for example by using packaging extracts commercially available from Stratagene, Inc. (La Jolla, Calif.) or Epicentre Technologies (Madison, Wis.). Mutations in the lac region of the shuttle vector can be conveniently detected in a host *E. coli* cell using procedures described in the BIG BLUE Transgenic Rodents Mutagenesis Assay System Instruction Manual (Stratagene, La Jolla, Calif.). Alternatively or additionally, mutations in the cII region of the shuttle vector can be conveniently detected in a host *E. coli* cell using procedures described in either the λ Select-cII Mutation Detection System for BIG BLUE Rodents Instruction Manual (Stratagene, La Jolla, Calif.) or described in written instruction materials that accompany the Epicentre Technologies (Madison, Wis.) kit.

The λLIZ shuttle vector (FIG. 1) includes the *E. coli* lacI gene as a mutation target and alacZ as the reporter gene. The system uses a forward mutation assay capable of detecting a wide spectrum of mutations in the lacI target. The lacI target is the most well-characterized target gene for mutagenesis, with more than 30,000 mutants identified in prokaryotic and eukaryotic cells (see, e.g., S. W. Kohler et al., *Proc. Natl. Acad. Sci. U.S.A.* 88:7958–7962 (1991). Following mutagen exposure, genomic DNA is isolated from the tissues of interest. The shuttle vector is recovered or "rescued" from the genomic DNA by in vitro packaging, preferably by utilizing TRANSPACK packaging extract (Stratagene, Inc., La Jolla, Calif.) which packages the vector into viable phage particles. Mutations in lacI are detected histologically in *E. coli,* as described below. The BIG BLUE lac-based assay system has been shown to detect most classes of mutations, including base substitutions, single-base frameshifts, insertions, duplications, and deletions (J. C. Mirsalis et al., *Ann. Rev. Pharmacol. Toxicol.* 35:145–164 (1995); G. S. Provostet al., *Mutation Res.* 288:133–149 (1993)).

Mutations that interfere with the lac repression lead to transcription of the alacZ region, allowing formation of intact LacZ protein, β-galactosidase, through alpha complementation within the bacterial host. Mutations are analyzed by isolating genornic DNA from the transgenic animal and recovering the shuttle vector as functional bacteriophage using in vitro packaging. The packaging extract is preferably free of all known restriction systems (restriction minus) and permits efficient recovery of the phage independent of DNA methylation as is known in the art. The individually packaged phage infect and lyse *E. coli* bacterial hosts that produce complementing portions of the LacZ protein. In the presence of a chromogenic substrate, functional mutations in lacI or the lac operator are seen as blue plaques on a lawn of clear nonmutant plaques. Mutant frequency is expressed as the ratio of the number of blue plaques to the total number of plaques tested. Each mutant can be further analyzed by sequence analysis of the lacI target gene without subcloning, using a modified polymerase chain reaction (PCR) method.

Alternatively, the cII gene in the λLIZ shuttle vector (FIG. 1) can serve as a mutation target. Selection of mutants in the λ Select-cII mutation detection system is based on the ability of bacteriophage λ to multiply through either the lytic or lysogenic cycle in *E. coli* host cells. The commitment to either lysis or lysogeny is made by lambda upon infection of an *E. coli* host cell and is regulated by a series of proteins, one of which is the product of the cII gene. Transcription of the cII gene is initiated at the $P_R$ promoter, and the cII gene is transcribed as part of a polycistronic message, which includes cro, O, P, and Q. At two lambda promoters, the cII protein activates transcription of genes essential for the lysogenic response. One of these promoters is $P_{RE}$, which is located within the 5' end of the cII gene in the orientation opposite to that of cII transcription. $P_{RE}$ establishes transcription of the gene for the cI repressor protein. The cI repressor protein binds to the $O_R$ operator, inhibiting transcription at $P_R$ and effectively shutting down transcription of several genes essential for the lytic response, committing the phage to the lysogenic cycle. In the λLIZ vector, the gene for the cI repressor protein contains the temperature-sensitive cI857 mutation that disables the cI repressor protein at 37° C., allowing titering in the preferred bacterial host strain (*E. coli* G1250). Thus, a detectable mutation in the cII gene either impairs the function of the cII protein or disables the $P_{RE}$ promoter of the cI gene, in either event preventing transcription of the cI gene. In the absence of the cI repressor protein, the phage multiply through the lytic cycle. In contrast, a nonmutant cII gene results in a functional cI repressor protein, and the phage genome undergoes lysogenization.

Mutation Analysis

A mutated target sequence can be subjected to nucleic acid sequencing to determine the mutation spectrum characteristic of a particular mutagen, or of a particular tissue, or of the action of a particular mutagen on a particular tissue. A mutation spectrum reflects the frequency of certain specific types of mutations in a population of mutants. Types of mutations include, for example, nucleotide transitions (G/C to A/T and A/T to G/C), nucleotide transversions (G/C to T/A, G/C to C/G, A/T to T/A, and A/T to C/G), and frameshift mutations (e.g., +1, +2, −1 and −2). Alternatively, mutations can be identified using single nucleotide polymorphism analysis, or any other method known in the art for identifying or detecting single site mutations, insertions, deletions and frameshifts.

The mutation spectrum of a population of mutants can provide much useful information. In some instances, the spectrum is characteristic of a particular mutagen or class of mutagens, and can help identify the nature of the mutagenic compound. In other instances, a change in the mutation spectrum, relative to the mutation spectrum of a control group, may be evident even though the differences in mutation frequencies (experimental vs. control) are not statistically significant. In still other instances, mutation spectrum analysis can yield information about the sensitivity of different organs or tissues to a particular mutagen.

EXAMPLES

The following examples, while exemplary of the present invention, are not to be construed as specifically limiting the invention. Accordingly, variations and equivalents, now known or later developed, that would be within the purview of one skilled in the art are to be considered to fall within the scope of this invention.

Example 1

Creation of a Transgenic Fish

The BIG BLUE Lambda Shuttle Vector λLIZ (Stratagene, Inc., La Jolla, Calif.; see the BIG BLUE Transgenic Rodent Mutagenesis Assay System Instruction Manual, specifically incorporated herein by reference, in its entirety) was used to create a transgenic medaka. Previous attempts to recover the λLIZ bacteriophage vector from both transgenic rodents and from fish that carry low gene copy numbers (e.g., 1–3 copies) have been problematic; it is highly desirable that transgenes are present at a level of several copies per cell or more to permit a high ratio of recovered target vector per genome (M. J. Dycaico et al., *Mutation Res.* 307:461–478 (1994)). Thus, efforts were made to increase the transgene copy number in the transgenic fish by creating a shuttle vector having multiple copies of the mutation target sequence. To this end, the λLIZ shuttle vector (about 50 kb) was cos-ligated, end to end, as linear concatamers. Specifically, the cos sites were melted by incubating λ DNA (50 μg) at 68° C. for 5 minutes, followed by ligation overnight (4° C.) with T4 ligase (0.5 mm ATP, 0.06 units/μl ligase, 1×ligase buffer, 714 ng/μl DNA) (New England Biolabs, Inc., Beverly, Mass.). DNA was brought up to 750 μl volume with STE (0.1 M NaCl, 10 mM Tris HCL, 1 mM ethylenediaminetetraacetic acid, EDTA, pH 8.0) and extracted twice with phenol/chloroform, once with chloroform, and precipitated with 100% ethanol. Following centrifugation, the pellet was washed with 70% ethanol, dried, and dissolved in TE (10 mM Tris, 1 mM EDTA, pH 8.0) at a DNA concentration of 100–200 ng/μl, determined by conventional spectrophotometric technique. The resulting construct, possibly hundreds of kb in size, is orders of magnitude larger than other vectors (typically about 5 kb) successfully used to create transgenic fish, such as ψX174 (R. Winn et al., *Marine Environ. Res.,* 40:247–265 (1995)). Prior to microinjection, the DNA was diluted to a concentration between 50–100 ng/μl in 5T.1E solution (5 mM Tris; 0.1 mM EDTA) and dialyzed on a filter (0.025 micron pore size, from Millipore, Bedford, Mass.) over 5T.1E for 40 minutes. Relatively large amounts of DNA were used in each of the injections to increase the likelihood of genomic integration.

Initially, 490 one-cell stage medaka embryos were injected with heterologous DNA. Heterologous DNA was microinjected into one-cell stage medaka embryos substantially according to the method of Winn et al. (*Marine Environ. Res.,* 40(3):247–265 (1995), as modified herein. To maximize incorporation of the heterologous DNA and possibly reduce the degree of mosaicism in the founders, fertilized eggs at the one-cell stage were collected by removing egg masses from the vent of the female fish beginning 2 hours prior to the onset of a 16-hour light cycle and every 10–15 minutes thereafter. The gene transfer method was optimized by rigidly controlling the timing of the injection at the earliest 1-cell stage of development of the fish, in most cases within 5 minutes of fertilization. The embryos were individually separated by removing the entangling chorionic fibrils and examined to verify the one-cell stage of development for efficient gene transfer. The one-cell embryos were placed within a watch-glass filled with 18‰ (parts per thousand salinity) seawater to better visualize the penetration of the injection needle and to reduce the incidence of fungal infection.

Injection of the heterologous DNA was performed with the aid of a dissection microscope, micromanipulators, and an $N_2$ pressurized gas injection apparatus (model PLI100 commercially available from Medical Systems Corp., Greenvale, N.Y.). The embryo was held in place with a capillary pipette (25 μm) secured with a micromanipulator. Another capillary pipette pulled to a fine tip (1–2 μm) secured by a micromanipulator, and attached to a gas injection apparatus served to inject the embryo. The DNA solution was injected through a continuously flowing pipette into the cytoplasm of the one-cell embryo, or through the micropyle if visible. This is in contrast to the technique used in rodents, wherein the DNA solution can be directly injected into the rodent cell nucleus. It is believed that injection through the micropyle is preferable since introduction into the cytoplasm may increase the likelihood of degradation of the DNA construct and, more important, may give rise to mosaic (or chimeric) integration of the gene in the tissues of a resultant transgenic fish. That is, not all of the cells will have the heterologous DNA integrated chromosomally. Mosaic integration of the transgene in transgenic fishes is very common and is problematic because germ-line transmission is not guaranteed even if DNA extracted from a fin clip (the typical assay for integration) indicates the founder fish carries the gene. The flow rate and the total amount of solution injected was controlled by adjusting the pressure of the gas and the duration of the injection which permitted injection of approximately 5–20 nl DNA solution.

Injected embryos were transferred into dechlorinated tap water and incubated therein using several different procedures. Some embryos were placed on 20 mm petri dishes, others were placed on cell culture plates, and others were placed in containers with air supply ("bubblers") to allow for constant aeration during growth at 26° C. until hatching (about 10 to 12 days). Embryos were examined daily and any dead were removed from the dishes. An earlier attempt was made that involved incubation in Yamamoto's solution (Yamamoto, "Medaka (killifish): Biology and Strains," Keigaku Publishing Co., Tokyo, Japan, 1975) for 5 days, and then in sterile culture water until hatching in approximately 10 days, however this procedure was discontinued after reduced survival in this solution was observed. A total of 141 fish survived in this initial experiment to age 6–8 weeks (28%) and were analyzed for the presence of heterologous DNA as described below. In a second experiment, a total of 238 fish (4–6 weeks post hatch) were analyzed in the same way.

Genetic screening for the presence of integrated λLIZ sequences and gene copy number evaluation of $F_1$ generation fish were simultaneously performed via PCR using a new instrument and DNA detection system. This accelerated the assessment of the positive $F_1$ generation fish which were not mosaic for integration of the transgene and therefore permitted the establishment of the specific high copy number lineages. The traditional method of copy number quantitation using Southern blot methods (described below) was not necessary.

Enhancements in the PCR method over the last decade have fostered the development of numerous and diverse applications. A recent enhancement facilitates real-time, quantitative analysis of the DNA amplification using fluorescence-based PCR. The analysis uses a DNA sequence detection instrument (ABI PRISM 7700 Sequence Detection System, Perkin Elmer Applied Biosystems, Foster City, Calif., USA) which combines PCR with a fluorogenic 5' nuclease assay. Pairs of primers (forward and reverse) 18–25 mer oligonucleotides that anneal within the DNA sequence of interest are synthesized in order to generate an amplified product generally ranging from 60–70 base pairs (bps) in size. A 20–30 mer oligonucleotide is synthesized as a probe to anneal within the PCR product generated by the forward and reverse primers. This fluorogenic, target-specific probe comprises an oligonucleotide with both a reporter and a quencher dye attached, and anneals to the target sequence between the forward and reverse primers. The probe typically includes a FAM (6-carboxy-fluorescein) reporter dye linked to the 5' end of the oligonucleotide and TAMRA (6-carboxy-tetramethylrhodamine) attached at the 3' end of the oligonucleotide as the quencher dye. As the PCR proceeds the probe is cleaved by the 5' nuclease activity of a DNA polymerase which permits the detection of the reporter dye signal. The DNA sequence-specific fluorescence signal is generated and detected in solution during the PCR. Assuming a 100% efficiency of amplification, the threshold cycle decreased by one cycle as the concentration of the template doubles. Therefore, the input DNA target quantity can be determined based on the cycle at which fluorescent signal is first detectable. The quantitative PCR analysis incorporates kinetic analysis in which the initial copy numbers of unknowns are determined by comparison with a curve generated from samples of known initial DNA quantities.

The typical conditions for the fluorescence-based PCR were as follows: 100 ng DNA; 4 mM $MgSO_4$; 200 M dATP, dCTP, dGTP; 400 uM dUTP; 125 M probe; 0.625 U Amplitaq Gold™ polymerase; 0.25 U Amerase UNG; and 1× of supplied buffer. A two stage amplification profile was used with 2 minutes at 50° C., 10 minutes at 95° C.; followed by stage two with 15 seconds at 95° C., 1 minute at 60° C. for a total of 30 cycles. A hold cycle at 25° C. was used following completion of amplification. Samples were prepared using sterile water in the place of DNA in the reagent mixture as no template DNA controls. Replicate serial dilutions of known quantities of DNA, were prepared to construct a standard curve from which the quantities of unknown samples were estimated.

In this example, screening for the presence of integrated λLIZ was accomplished prior to copy number determination using a standard PCR assay on DNA isolated from excised fin tissue. Genomic DNA is extracted from caudal fin tissue excised from presumptive transgenic fish aged 1–2 months. The DNA is extracted by homogenization of the tissue in 0.3 mL 1×SSC (150 mM NaCl, 15 mM sodium citrate; see page B.13 of Sambrook et al., Molecular Cloning, a Laboratory Manual, $2^{nd}$ Ed., Cold Spring Harbor Laboratory Press, 1989), 0.5% sodium dodecyl sulfate, SDS, and 10 mg/mL proteinase K for 3 hours at 55° C. Samples were extracted twice with methylene chloride:isoamyl alcohol (24:1) containing 0.1 5 M NaCl, precipitated with two volumes 100% ethanol and resuspended in TE buffer (10 mM Tris, 1 mM EDTA pH 8.0). The DNA concentration is then estimated by measurement of absorbence at 260 nm. Several lacI sequencing primer pairs (commercially available under the trade designation BIG BLUE lacI PCR Primer Set, from Stratagene, La Jolla, Calif.) can be used to generate PCR products of about 200–800 kb. A standard amplification temperature profile is: initial denaturation 95° C., 60 seconds; denaturation 95° C., 30 seconds; annealing 60° C., 30 seconds; and extension 72° C., 60 seconds. When using this screening method, we utilized two oligonucleotide primers, "Lambda 1" (5'-GAT GAG TTC GTG TCC GTA CAA CTG G, SEQ ID NO:4) and "Lambda 2" (5'-GGT TAT CGA AAT CAG CCA CAG CGC C-3', SEQ ID NO:5), and PCR conditions of initial denaturation 94° C., 30 seconds; denaturation 60° C., 30 seconds; extension 72° C., 60 seconds, for 30 cycles. Electrophoresis of the PCR products on an agarose gel (1–2%) can be used to confirm amplification of the DNA fragment of appropriate size. In previous experiments, integration rate in founder ($F_0$) transgenic medaka has typically been approximately 7–10%; however using the procedures set forth in this example, the integration rate jumped to 16%.

In this alternative method, copy number determination can be accomplished using a Southern blot hybridization using a biotinylated λLIZ DNA probe and chemiluminescent detection. Genomic DNA (5–10 µg) from previously PCR-screened positive transgenic fish is digested with HindIII in the presence of 4 mM spermidine to improve digestion, followed by electrophoresis on a 0.8% agarose gel and then transfer to a nylon membrane using conventional biotechnological techniques. The membrane is baked at 80° C. for 30 minutes and exposed to a UV transilluminator for 5 minutes. Prehybridization is performed at 42° C. for 1 hour in a 20 mM sodium phosphate buffer (pH 7.5) containing 50% formamide, 5×SSC, 5×Denhardt's solution (Sigma Chemical Company, St. Louis, Mo.), 0.1% SDS and 100 µg/mL denatured calf thymus DNA. Hybridization is performed at 42° C. for 16 hours with about 20 ng of a biotinylated λLIZ DNA probe. Membranes are washed twice for 5 minutes at 20° C. in 2×SSC, 0.1% SDS, and twice for 15 min at 68° C. in 0.2×SSC, 0.1% SDS. Membranes are analyzed by chemiluminescent detection according to the manufacturer's detection protocol with film exposures of 20–60 minutes (commercially available under the trade designation PHOTOTOPE CHEMILUMINESCENT DNA DETECTION KIT, from New England Biolabs, Beverly, Mass.). Copy number standards, prepared by adding λLIZ DNA (equivalent to 1–50 copies per genome) to calf thymus DNA (5 µg), are loaded adjacent to the DNA from presumptive transgenic fish. Copy number estimates can be made by using the DNA content of 2.2 pg for the diploid genome of medaka.

From the initial experiment, 9 of the 141 founders were shown to have incorporated the µLIZ vector, and of these 9, two showed germline transmission. Likewise, in the second experiment, 53 of the 238 founders were shown to have incorporated the vector, and 13 of the 53 showed germline transmission. Together, a total of 62 fish (16% of the founder population) showed positive amplification of the λLIZ product of the appropriate size (~50 bp), and 15 of those showed germline transmission (24%). The transgenic founders that showed germline transmission when mated with wild-type mates transmitted the DNA sequence to their offspring at frequencies of 3–40% (Table 1). The observed gene transfer frequency represents an improvement over previous efforts, and ranks among the highest reported in other transgenic fish efforts. The variable frequencies of gene transmission to $F_1$ offspring demonstrated the mosaic germ-line integration characteristic of transgenic fish.

Gene copy number results for the selected members of this transgenic founder population are also shown in Table 1. Of eleven transgenic lineages analyzed, five lineages carry 2 copies, including one lineage (#310) that carries in excess of 75 copies.

TABLE I

Estimated gene copy number and frequency of germ-line transmission for selected transgenic λLIZ medaka lineages

| Founder lineage frequency | Copy number | Germ-line transmission |
| --- | --- | --- |
| 013 | 1 | 35% |
| 108 | 1 | 3% |
| 188 | 1 | 20% |
| 203 | ~4–5 | 13% |
| 254 | 1 | 40% |
| 261 | ~3–4 | 20% |
| 304 | 1 | 36% |
| 310 | >75 | 12% |
| 327 | ~1 | 5% |
| 361 | ~2 | 10% |
| 370 | ~2 | 29% |

Following confirmation of positive integration of λLIZ in the $F_1$ generation, the transgenic siblings were bred to produce $F_2$ generation fish. The quantitative fluorescence-based PCR procedures described above facilitated distinguishing the homozygous and hemizygous transgenic $F_2$ generation fish, thereby speeding the establishment of homozygous lines by eliminating the need to perform time-consuming traditional methods that rely on DNA hybridization techniques (i.e. Southern blots). Homozygous status was verified genetically by crossing presumptive homozygous fish with wild-type fish, in which case the presence of 100% positive transgenic offspring confirmed homozygous status. In addition, by using these quantitative fluorescence-based PCR procedures, transgenic lineages that carry multiple copies of the vector, and therefore have the greatest promise for efficient recovery of the vector, were identified.

These results compare favorably to those obtained from producing transgenic rats with the identical mutation target. In this effort, 62 transgenic founders were obtained out of a total of 379 injected embryos that survived to an age of 6–8 weeks, or 16%. For the transgenic rat study, over 12,000 Fisher 344 inbred rat embryo injections produced 257 surviving pups and resulted in 17 transgenic founders, or 6.6% (M. J. Dycaico et al., *Mutation Res.* 307:461–478 (1994)). Although the majority of these 17 rodent founders carried less than 5 copies of λLIZ, two founders carried more than 20 copies, such that homozygous individuals of subsequent generations carried at least 40 copies. Attempts to recover the vector from λLIZ transgenic rats that carried only 1–2 gene copies was not possible in several lineages, and, in other low copy number lineages from which recovery was possible, the low rescue efficiencies increased the time and costs of analyses as compared to those for higher copy number animals.

Example 2
Recovery of λLIZ Shuttle Vector

Fish tissues appear to pose a significant problem related to efficient recovery of bacteriophage and plasmid-based vectors for mutation detection. The extraction of high quality and high molecular weight genomic DNA is very important to the efficient recovery of the shuttle vector from transgenic rodent tissues. However, repeated attempts to recover shuttle vectors from transgenic fish tissues using the procedures developed for rodents have in the past been unsuccessful.
Isolation of Genomic DNA Initial recovery of the shuttle vector was attempted using DNA obtained from two homozygous fish lineages that carried only ~1–2 copies of the vector (lines #13 and 108, Table I). The vector recoveries from these fish were unsuccessful. Vector recovery from animals which carry low copy numbers has previously been shown to be problematic in transgenic rodent studies. Therefore, transgenic fish that had relatively high gene copy numbers (>5–10 copies) and demonstrated stable germ-line transmission were selected for the analysis of recovery and spontaneous mutation frequency of λLIZ. In addition, standard procedures for isolating genomic DNA from rodents were altered so as to insure isolation of high quality genomic DNA sufficient for recovering shuttle vectors from the fish, as described below.

Transgenic $F_1$ generation fish (4–6 weeks old, line #310, hemizygous for ~100 copies) were either flash frozen in liquid nitrogen or quickly minced prior to placing in a dounce homogenizer containing 2 mL douncing buffer (1×SSC, 1% SDS). Fish were dounced twice only and transferred to a centrifuge tube. An additional 3 mL of dounce buffer was added to the centrifuge tube, and freshly made Proteinase K solution (150 μL, 20 mg/mL) was then added as well. Samples were placed at 37° C. for 1½ hours. Tubes were inverted two times at 30 minute intervals. Samples were extracted with 5 mL 50:50 buffered phenol:chloroform by inverting 5 times followed by centrifugation at 4000 rpm for 10 minutes. Supernatant was placed in a clean centrifuge tube and the phenol:chloroform extraction, including the centrifugation, was repeated. The supernatant was again removed, and 8M potassium acetate was added thereto to a final concentration of 1M. An equal volume of chloroform was also added, the tubes were inverted gently, and were then centrifuged as before. Supernatant was removed to a clean tube to which two volumes of 100% ethanol were added. Tubes were inverted gently several times and allowed to sit at room temperature (about 22° C.) for 10 minutes. Precipitated DNA was spooled with a flame-sealed Pasteur Pipette, dried in air, and resuspended in 50–100 μL TE buffer (Tris 10 mM, EDTA, 1 mM, pH 7.5). Importantly, this protocol incorporates a shorter digestion time (1½ hours) at a lower temperature (37° C.) compared to the standard procedure used to isolate genomic DNA from mice (wherein the digestion is carried out at 50° C. to 55° C. for 3 hours), thus enhancing the recovery of assayable genomic DNA from the fish.

It should be noted that this DNA extraction method can be used to recover DNA directly from an organ or a tissue of a fish. The protocol is typically carried out using reduced volumes (since the amount of biological material to be extracted is reduced), and the ethanol-precipitated DNA can be isolated by centrifugation rather than by spooling. This method offers great benefit in that it allows for the study of tissue-specific mutation frequencies.

Packaging Reaction

From these genomic fish DNAs, the λLIZ vector was recovered and packaged into empty phage particles creating infective phage according to the protocols recommended by the manufacturer for in vitro packaging (TRANSPACK in vitro packaging extract, Stratagene, La Jolla, Calif.). Specifically, the packaging extract was added to 8 μl of genomic DNA (>0.5 mg/mL), incubated at 30° C. for 90 minutes, at which time the packaging reaction was terminated by adding SM buffer.

Infection of Bacterial Host and Screening: λ—Select cII Assay

Figure 3:
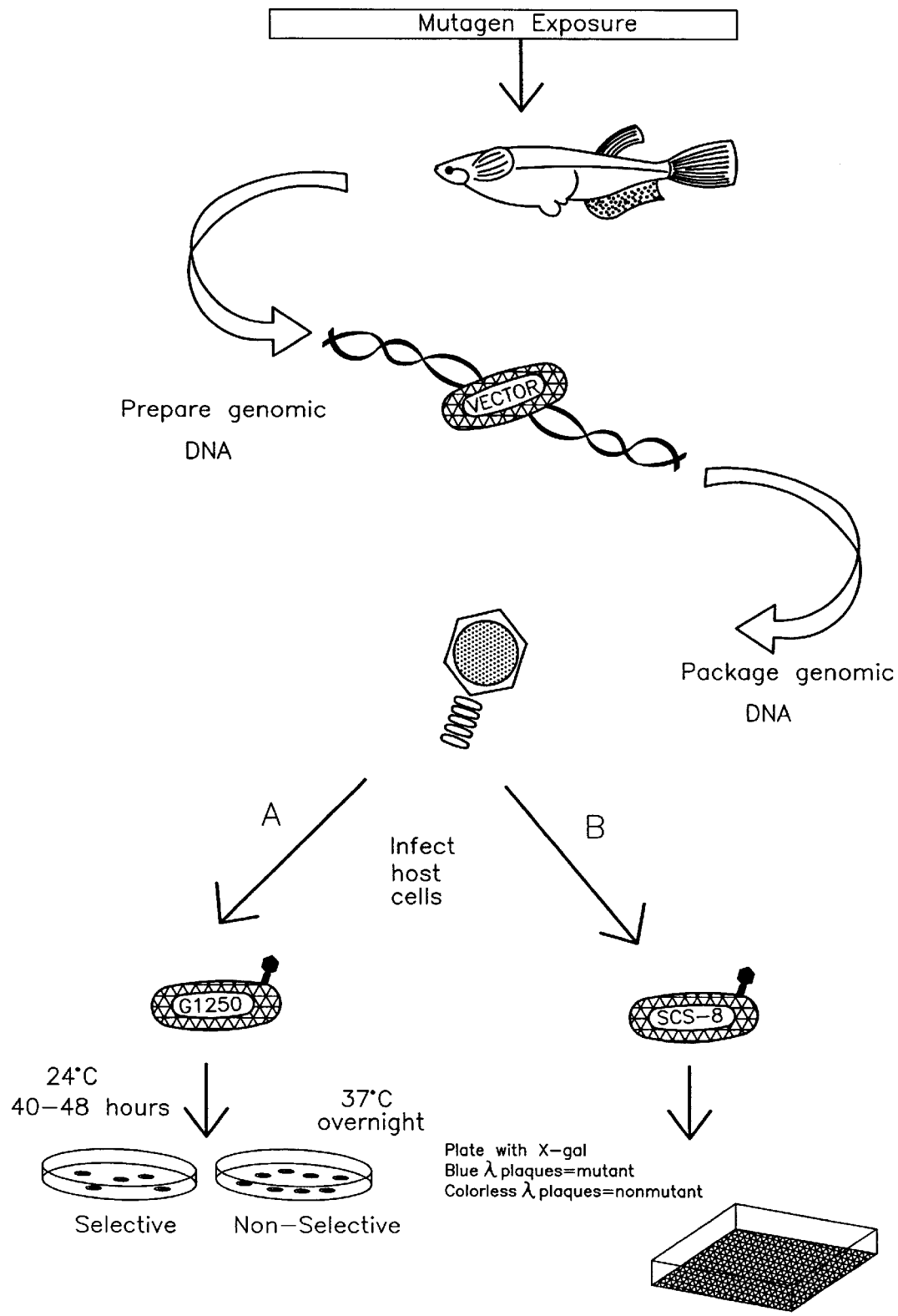
FIG. 3 is schematic diagram that illustrates selection assays based on the mutations in the (A) cII region and the (B) lac region of the BIG BLUE λLIZ shuttle vector shown in FIG. 1.

The individually packaged lambda phage were used to infect the *E. coli* host strain G1250 (see FIG. 3A). The G1250 plating cell culture was mixed with diluted (titer) and undiluted packaged DNA (mutant screening). Titer plates were placed at 37° C. overnight, and screening plates were placed at 24° C. for 40 hours. A 40 hour incubation is preferred to the recommended 48 hour incubation to reduce mottling on the plates. Because the λLIZ shuttle vector contains the temperature-sensitive cI857 mutation, $\lambda^+$ multiply through the lytic cycle under the nonselective conditions, resulting in plaque formation. The rescue efficiency was determined by averaging the number of plaques on the three titer (dilution) trays and computing the total number of plaques obtained per packaging reaction. The spontaneous mutation frequency was calculated by dividing the number of confirmed mutants by the estimated total number of plaques recovered.

An average of 2,060,000±65,000 plaques were recovered from a single packaging reaction of line 310 hemizygous fish, indicating very high efficiency in the recovery of the phage. Table II shows the relationship between copy number and phage recovery, showing that attempts to recover the phage from low copy number lineages were not successful. Recovery was achieved from lines 203 and 310, with line 310 exhibiting exceptional efficiency, particularly in comparison to the 625,000 plaques recovered from Big Blue mouse DNA analyzed simultaneously. A minimum of 300,000 plaques is recommended for statistical purposes.

TABLE II

Relationship of copy number and efficiency of λ recovery

| Founder lineage | Copy number | Recovery (pfu) |
|---|---|---|
| 13 | 1 | none |
| 108 | 1 | none |
| 188 | 1 | (1) |
| 203 | 4–5 | $0.05 \times 10^5$ |
| 254 | 1 | (1) |
| 261 | 3–4 | none |
| 304 | 1 | (1) |
| 310 | >75 | $3\text{-}16 \times 10^5$ |
| 370 | 2 | none |

(1) Phage rescue was not attempted from these samples.

Infection of Bacterial Host and Screening—lac Assay

Individually packaged lambda phage from four of the fish (lineage 310) were absorbed onto *E. coli* SCS-8 cells (commercially available from Stratagene), mixed with top agarose (NZY medium) with 0.7% agarose) containing (1.5 mg/mL) 5-bromo-4-chloro-3-indolyl-β-D-galactopyranoside (X-gal) and plated onto 25×25 cm square bioassay trays containing 250 mL NZY bottom agar (NZY medium with 1.5% agar) (see FIG. 3B). Packaged control λ were plated on VCS-257 cells using serial dilutions. Alternatively, the absorbed phage mixture can be sampled, diluted and plated in duplicate or triplicate as plating efficiency plates to determine the total number of phage per packaging reaction kit. The number of plates per packaging reaction was adjusted to give a target packaging density of about 15,000 plaques per plate (24 plaques/cm$^2$). Experiments included color control plates using a series of lacI mutants that produce a spectrum of color intensities from very faint (CM-0) to intense dark blue (CM-3). Plates were incubated for 16–18 hours at 37° C.

After incubation, plates were visually screened for blue mutant plaques using a red enhancement screening filter. The total number of plaques was counted on plating efficiency plates to calculate total plaques screened. The efficiency of the packaging extract was determined by counting the plaques on control λ plate. Bacterial lawn and plaques are blue because VCS257 contains and expresses the intact lacZ gene.

The efficiency of the packaging extract was determined by:

$$\frac{(\text{\# of plaques}) X (\text{dilution factor}) \times (\text{total packaging volume})}{(\mu g \text{ control } \lambda) \times (\mu g \text{ plated})} = \text{pfu/mg DNA}$$

and was expressed as plaque forming units (pfu) per mg DNA.

The rescue efficiency was determined by averaging the number of plaques on the dilution trays and computing the total number of plaques obtained per packaging reaction. A total of over 500,000 pfu were recovered from each of the four samples. The efficiency of the recovery can be evaluated and related to the amount of DNA necessary to obtain a recommended 300,000–500,000 plaque forming units (pfu)/analysis.

Example 3

Mutagen Exposure Experiments

Mutagens

N-ethyl-N-nitrosourea (ENU) is a well-characterized mutagen and carcinogen that acts by direct ethylation of oxygen and nitrogen in the bases of DNA (B. Singer, *Nature* 264:333–339 (1976)); B. Singer et al., *Nature* 276:85–88 (1978)). ENU is a useful agent for the study of the relationship of mutation to DNA repair, replication, adduct persistence, and cell differentiation (J. G. Burkhart et al., *Mutation Res.* 292:69–81 (1993)). A limited study of ENU-induced mutation has been previously performed using medaka (A. Shimada et al., *Zoological Sci.* (*Tokyo*) 8(6):1127 (1991); A. Shimada et al., *Zoological Sci.* (*Tokyo*) 7(6):1053 (1990)).

Dimethylnitrosamine (DMN) is a methylating agent and potent liver carcinogen in mice (International Agency for Research on Cancer (IARC), IARC Monographs on the Evaluation of the Carcinogenic Risk of Chemicals to Humans, Vol. 7, IARC, Lyon. 253p (1974)). Since cell proliferation is an important parameter for the induction of mutations, it is important to consider the influence of fixation time of adducts on the induction of mutations. DMN has been used as a representative mutagen which forms methylated DNA adducts in transgenic mice (J. C. Mirsalis et al., *Mutagenesis* 8:265–271 (1993)). DMN is among the nitrosamines that have induced hepatocarcinogenesis in fish with progressive stages similar to those characterized in rodent hepatic neoplasia (W. E. Hawkins et al., Chapter 14 in G. M. Rand, ed., Fundamentals of Aquatic Toxicology: Effects, Environmental Fate, and Risk Assessment, Taylor and Francis. 421–446 (1995)).

Exemplary Exposure Regimen

Fish mutagen exposure is performed by using protocols employed in previous transgenic rodent studies (e.g., M. J. Dycaico et al., *Mutation Res.* 307:461–478 (1994); B. J. Rogers et al., *Mutation Res.* 327:57–66 (1995)). Specifically, one regimen consists of a single-pulse 4 hour exposure; another consists of a multiple-pulse exposure regimen consisting of 2 pulses for a 4 hour exposure for 7 days. Prior to final exposure, range-finding assays for each of the two model compounds are conducted wherein fish are exposed in single-pulse and multiple-pulse treatments over a range of mutagen concentrations to determine the upper exposure concentration expected to produce minimal or zero lethality (about 50% of the lowest exposure concentration at which deaths occur). In previous mutagen exposure studies using λLIZ transgenic mice, doses of 50–250 mg/kg of ENU ($LD_{50}$~350 mg/kg) were used to obtain at least a two-fold mutation frequency induction. The range finding trials in the present example are 0, 25, 50 and 100 ppm of ENU and DMN.

Fish are placed in replicated 40 mL acid-washed borosilicate glass test chambers (20/chamber). The mutagen solutions, at concentrations determined by dilution factors, are added to water immediately prior to the initiation of exposure. Toxicant-free treatments accompany all exposures as controls. For the multiple-pulse regimen, fish are transferred and held in clean water to await the next exposure. The fish are not fed during the exposure period. During the exposure phase, fish are monitored regularly for any visual signs of distress. Any dead or moribund fish are removed.

Following the final exposure series, fish are rinsed and transferred to grow-out aquaria for a prescribed expression time. During this time fish are held in aquaria in toxicant-free water at 26° C. on a 12:12 hour light:dark regime and fed twice daily. The fish are visually monitored at least twice daily during feeding. Any fish that have died, or that exhibit abnormal swimming behaviors or other visible signs of distress, are be removed from the aquaria. Fish that show apparent formation of external neoplasms are removed, sacrificed, and saved for further analyses, if desired.

The influence of expression time on the mutation frequency is evaluated by sampling fish at 5, 10, and 15 days following exposure. Expression time, or fixation time, is defined as the time allowed between dosing and sacrificing the animals for mutation assays. Some expression time is required, especially after single-dose administrations, to permit uptake and distribution of the chemical, metabolic activation to a DNA-reactive form, formation of adducts, and at least one cell division to "fix" the adduct as a heritable mutation. Although there is no data currently available on mutations rates, DNA repair, or cell proliferation in transgenic medaka, it is believed that a long expression time (>7 days) would allow adequate time to either repair DNA adducts or fix adducts as mutations. This reduces the possibility the DNA adducts will be mutated by the host *E. coli* by decreasing the number of DNA adducts present on the recovered target DNA.

ENU Exposure and Analysis

Medaka (50 hemizygous male and female, 4–8 weeks old) were exposed to 100 ppm and 200 ppm ENU for 1 hour in dechlorinated tap water in replicate 500 mL beakers. They were then transferred to clean water (no ENU) and held for 15 days. At that point the fish were quickly sacrificed using an overdose of MS-222 (tricaine methanesulfonate), flash frozen in liquid nitrogen, and stored at −70° C.

Mutagenesis in experimental and control fish was analyzed using the cII assay system as described in Example 2. The results in Table III show a greater than two-fold increase in cII mutations in the 100 ppm-exposed fish compared to the control fish, and an induced mutation frequency in the 200 ppm-exposed fish of nearly four times that of the controls. The overall spontaneous mutation frequency was determined to be $2.92 \pm 0.68 \times 10^{-5}$ for the cII target.

TABLE III

N-Nitroso-N-Ethylurea (ENU) Exposure Summary

|  | Recovery ($\times 10^6$) pfu | Number of Mutants | Mutation Frequency ($\times 10^{-5}$) |
|---|---|---|---|
| Controls | 3.03 | 97 | 3.20 |
|  | 2.37 | 58 | 2.45 |
|  | 1.62 | 58 | 3.59 |
|  | 1.91 | 64 | 3.35 |
|  | 2.38 | 42 | 1.76 |
|  | 2.4 | 76 | 3.17 |
|  |  |  | X = 2.92 ± 0.68 |

TABLE III-continued

N-Nitroso-N-Ethylurea (ENU) Exposure Summary

|  | Recovery ($\times 10^6$) pfu | Number of Mutants | Mutation Frequency ($\times 10^{-5}$) |
|---|---|---|---|
| 100 ppm | 1.79 | 129 | 7.21 |
|  | 2.31 | 118 | 5.11 |
|  | 1.64 | 125 | 7.65 |
|  | 1.70 | 114 | 6.73 |
|  | 2.48 | 243 | 9.80 |
|  | 1.28 | 149 | 11.67 |
|  |  |  | X = 8.03 ± 2.34 |
| 200 ppm | 1.79 | 159 | 8.88 |
|  | 3.95 | 399 | 10.10 |
|  | 1.56 | 133 | 8.55 |
|  | 1.73 | 198 | 11.48 |
|  | 1.60 | 341 | 21.27 |
|  | 1.54 | 176 | 11.45 |
|  |  |  | X = 11.96 ± 4.7 |

Similar results (a two-fold increase) were observed for the lacI target in the 100 ppm-exposed fish. A spontaneous mutation frequency for the lacI target was calculated by dividing the number of confirmed mutants (blue plaques) by the estimated total clear plaques, and determined to be about about $1.01 \times 10^{-5}$. For comparison, the spontaneous mutation frequency of the identical λLIZ mutation target in transgenic mice and rat tissues has been determined to be $2-4 \times 10^{-5}$ (G. S. Provost et al., *Mutation Res.* 288:133–149 (1993); M. J. Dycaico et al., *Mutation Res.* 307:461–478 (1994)).

Example 4

Mutation Analysis of the cII Target Gene

Putative mutant plaques were verified by coring and re-plating them with *E. coli* G1250 to confirm phenotypic stability of the mutant. Selected mutations were analyzed by sequence analysis of the cII target gene using linear amplification sequencing in which the components of a chain-termination sequencing reaction were cycled through a standard PCR temperature profile as described in the λ SELECT-cII Mutation Detection System for BIG BLUE Rodents instruction manual, Catalog #72010, Revision #028001. The cII target region from a purified λcII mutant was amplified by PCR using λ SELECT-cII sequencing primers, commercially available from Stratagene, La Jolla, Calif. Briefly, a plaque was transferred to a microcentrifuge tube containing 25 μL autoclaved dH₂O. The tube was capped securely and placed in boiling water for 5 minutes, then centrifuged at maximum speed for 3 minutes. The supernatant (10 μL) was immediately transferred to 40 μL of a PCR mastermix such that the final concentrations of the reagents were 1×Taq polymerase reaction buffer, 10 pmol of each primer, 12.5 nmol of each dNTP, and 2.5 U of Taq2000 DNA polymerase. The amplification reaction was overlayed with a drop of sterile mineral oil and the template was amplified using the following cycling parameters: a 3 minute denaturation at 95° C., followed by 30 cycles of 30 seconds at 95° C., 1 minute at 60° C., and 1 minute at 72° C., with a final extension of 10 minutes at 72° C. The products (2–4 μl) were loaded on a sequencing gel and analyzed for sequence differences; the results are shown in Table IV.

TABLE IV

| Mutation | % Spontaneous | ENU induced % |
|---|---|---|
| Transitions |  |  |
| G/C → A/T | 25 | 25 |
| A/T → G/C | 15 | 24 |
| Transversions |  |  |
| G/C → T/A | 20 | 14 |
| G/C → C/G | 10 | 14 |
| A/T → T/A | 5 | 19 |
| A/T → C/G | 0 | 0 |
| Frameshift (−1) | 20 | 5 |
| (+1) | 5 | 0 |

Example 5

Mutation Analysis of the lacI Target Gene

Putative mutant plaques can be verified by coring and re-plating them with *E. coli* SCS-8 on X-gal-containing medium to confirm phenotypic stability of the mutant. Selected mutations can be analyzed further by sequence analyses of the lacI target gene using the linear amplification sequencing which is a variation of the polymerase chain reaction (commercially available from Stratagene, Inc., La Jolla, Calif.) under the trade designation BIG BLUE CYCLIST Exo-Pfu). The components of a chain-termination sequencing reaction are cycled through a temperature profile consisting of a heat-denaturation step, an annealing step and an extension step, as described below.

Mutant plaques can be verified and isolated from non-mutant plaques re-plating in the presence of X-gal. LacI template DNA can be prepared for sequencing by PCR using the mutant λ phage directly as the template or by further purification (See Gu et al. *Mutation Res.*, 307:533–540 (1994)). The sequencing reaction mixture can be prepared as follows: 200 fmol template DNA, 1 pmol of primer (commercially available under the trade designation of BIG BLUE lacI PCR Primer Set, from Stratagene), 4 μl of 10×sequencing buffer, 10 μCi of radioactive label, 1 μl (2.5 U) of polymerase, water to 26 μl and 4 μl DMSO to a final volume of 30 μl. The mixture is cycled through a temperature profile of denaturation 95° C., 5 minutes; annealing 60° C., 30 seconds; and extension 72° C., 60 seconds. The products (2–4 μl) are loaded on a sequencing gel and analyzed for sequence differences. The sequence information on lacI as a target for mutagenesis suggests that many of the sites for inactivation of the lacI have been identified. Comparisons can be made with the type, number and percentage of mutations identified.

|  | Sequence Listing Free Text |
|---|---|
| SEQ ID NO: 1 | Portion of the BIG BLUE λLIZ Shuttle Vector, Stratagene, La Jolla, CA |
| SEQ ID NO: 2 | cII protein |
| SEQ ID NO: 3 | cII gene |
| SEQ ID NO: 4 | Oligonucleotide |
| SEQ ID NO: 5 | Oligonucleotide |

The complete disclosures of all patents, patent applications, publications, database entries, submissions and deposits, including GENBANK deposits and the descriptive information associated therewith, and other documents cited herein are fully incorporated herein in their entireties by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A transgenic fish whose genomic DNA comprises a recoverable assayable mutation target nucleic acid sequence operably linked to a bacteriophage lambda-derived transgene construct; wherein the mutation target nucleic acid sequence is recoverable from the transgenic fish, transferable into a bacterial host, and assayable in the bacterial host for the presence of a mutation.

2. The transgenic fish of claim 1 wherein the assayable mutation target nucleic acid sequence comprises at least one nucleic acid sequence selected from the group consisting of the lacI gene, the lacZ gene, the lac promoter sequence, the cII gene, the cII mRNA ribosome binding site and the cII protein-activated $P_{RE}$ promoter sequence.

3. The transgenic fish of claim 2 wherein the assayable mutation target sequence comprises the lacI gene.

4. The transgenic fish of claim 2 wherein the assayable mutation target sequence comprises the cII gene.

5. The transgenic fish of claim 1 wherein the assayable mutation target sequence comprises the cII region of bacteriophage lambda.

6. The transgenic fish of claim 1 wherein the bacteriophage lambda-derived transgenic construct comprises at least one cos site.

7. The transgenic fish of claim 1 wherein said fish is a teleost fish.

8. The transgenic fish of claim 7 wherein said fish is selected from the group consisting of a medaka, a zebrafish, a mummichog, a killifish, a channel catfish, a common carp and a trout.

9. The transgenic fish of claim 1 wherein said fish is sterile.

10. The transgenic fish of claim 1 that is hemizygous for the mutation target nucleic acid sequence.

11. The transgenic fish of claim 1 that is homozygous for the mutation target nucleic acid sequence.

12. A method for detecting mutations in the DNA of a transgenic fish comprising:
   providing a transgenic fish whose genomic DNA comprises a recoverable assayable mutation target nucleic acid sequence operably linked to a bacteriophage lambda-derived transgene construct;

recovering genomic DNA comprising the mutation target nucleic acid operably linked to the bacteriophage lambda-derived transgene construct;

transferring the genomic DNA into a bacterial host; and bioassaying in the bacterial host for the presence of a mutation in the mutation target nucleic acid sequence.

13. The method of claim 12 wherein the recovering step comprises extracting the genomic DNA from the fish to yield extracted genomic DNA comprising bacteriophage lambda-derived DNA comprising the assayable mutation target nucleic acid sequence and chromosomal DNA.

14. The method of claim 13 wherein the recovering step further comprises packaging the bacteriophage lambda-derived DNA to yield packaged phage.

15. The method of claim 14 wherein the transferring step comprises introducing the packaged phage into a bacterial host.

16. The method of claim 15 wherein the mutation target nucleic acid sequence comprises at least one nucleic acid sequence selected from the group consisting of the cII gene, the cII mRNA ribosome binding site and the cII protein-activated $P_{RE}$ promoter sequence of bacteriophage lambda.

17. The method of claim 16 wherein the bacterial host comprises an hfl$^-$ E. coli strain.

18. The method of claim 15 wherein the mutation target nucleic acid sequence comprises at least one nucleic acid sequence selected from the group consisting of the lacI gene, the lacZ gene and the lac promoter sequence.

19. The method of claim 16 wherein the bacterial host comprises an E. coli strain that produces a polypeptide that complements the polypeptide encoded by the alacZ region of the lacZ gene to form active β-galactosidase.

20. The method of claim 12 wherein the providing step comprises providing a transgenic fish that has been or is suspected of having been exposed to a mutagen.

21. The method of claim 12 further comprising exposing the transgenic fish to a mutagen prior to recovering the DNA comprising the mutation target nucleic acid sequence.

22. The method of claim 21 wherein the mutagen is selected from the group consisting of a chemical, a radio-isotope and electromagnetic radiation.

23. The method of claim 22 further comprising analyzing the mutation in the mutation target nucleic acid sequence.

24. The method of claim 23 wherein analyzing the mutation comprises determining the nucleic acid sequence of the mutation target nucleic acid sequence.

25. A method for evaluating the mutagenicity of a suspected mutagen comprising:

exposing a transgenic fish to a suspected mutagen, wherein the genomic DNA of the transgenic fish comprises a recoverable assayable mutation target nucleic acid sequence operably linked to a bacteriophage lambda-derived transgene construct;

recovering genomic DNA comprising the mutation target nucleic acid sequence operably linked to the bacteriophage lambda-derived transgene construct;

transferring the genomic DNA into a bacterial host; and bioassaying in the bacterial host for the presence of a mutation in the mutation target nucleic acid sequence.

26. The method of claim 25 wherein the mutation target nucleic acid sequence comprises at least one nucleic acid sequence selected from the group consisting of the lacI gene, the lacZ gene, the lac promoter sequence, the cII gene, the cII mRNA ribosome binding site and the cII protein-activated $P_{RE}$ promoter sequence.

27. The method of claim 25 further comprising analyzing the mutation in the mutation target nucleic acid sequence.

28. The method of claim 27 wherein analyzing the mutation comprises determining the nucleic acid sequence of the mutation target nucleic acid sequence.

29. The method of claim 27 wherein analyzing the mutation comprises determining a mutation spectrum of the suspected mutagen.

30. A method for making a transgenic fish for mutagenesis detection, said method comprising microinjecting heterologous DNA into a one-cell fish embryo, and incubating the microinjected embryo such that the embryo develops into a fish, wherein the heterologous DNA comprises a recoverable assayable mutation target nucleic acid sequence operably linked to a bacteriophage lambda-derived transgene construct, the mutation target nucleic acid sequence being capable of being recovered, transferred into a bacterial host, and bioassayed in the bacterial host for the presence of a mutation.

31. The method of claim 30 wherein the mutation target nucleic acid sequence comprises at least one nucleic acid sequence selected from the group consisting of the laci gene, the lacZ gene, the lac promoter sequence, the cII gene, the cII mRNA ribosome binding site and the cII protein-activated $P_{RE}$ promoter sequence.

32. The method of claim 30 wherein the heterologous DNA is microinjected through the micropyle within about 5 minutes following fertilization.

33. A mutagenesis assay system comprising:

a transgenic fish whose genomic DNA comprises a recoverable assayable mutation target nucleic acid sequence operably linked to a bacteriophage lambda-derived transgene construct; and a bacterial cell bioassay system for use in detecting the presence of a mutation in the target nucleic acid sequence that has been recovered from the transgenic fish after exposure to a potential mutagen, the bacterial cell bioassay system comprising a bacterial cell into which the target nucleic acid sequence has been introduced.

34. The mutagenesis assay system of claim 33 wherein the mutation target nucleic acid sequence comprises at least one nucleic acid sequence selected from the group consisting of the lacI gene, the lacZ gene, the lac promoter sequence, the cII gene, the cII mRNA ribosome binding site and the cII protein-activated $P_{RE}$ promoter sequence.

35. The mutagenesis assay system of claim 33 wherein the transgenic fish is sterile.

* * * * *

UNITED STATES PATENT AND TRADEMARK OFFICE
CERTIFICATE OF CORRECTION

PATENT NO. : 6,307,121 B1
DATED : October 23, 2001
INVENTOR(S) : Richard N. Winn It is certified that error appears in the above-identified patent and that said Letters Patent is hereby corrected as shown below:

<u>Title page,</u>
Item [56], References Cited, OTHER PUBLICATIONS,
Amanuma et al. reference, please delete "Detectig" and insert -- Detecting -- therefor.
Black reference, please delete "Carcinogenesis" and insert -- Carcinogenic -- therefor.
Gallagher et al. reference, please delete "Demethylbenz" and insert -- Dimethylbenz -- therefor.
Schwarz et al. reference, please delete "o" and insert -- O -- therefor.
http://www.stratagene.com/vol110 3/figures/p100-101.htm reference, please delete "γLIZ" and insert -- λLIZ -- therefor.

<u>Column 27,</u>
Line 33, please delete "alacZ" and insert -- α*lac*Z -- therefor.

<u>Column 28,</u>
Line 30, please delete "laci" and insert -- *lac*l -- therefor.

Signed and Sealed this

Third Day of September, 2002

Attest:

JAMES E. ROGAN
Attesting Officer   Director of the United States Patent and Trademark Office

SEQUENCE LISTING

<160> NUMBER OF SEQ ID NOS: 5

<210> SEQ ID NO 1
<211> LENGTH: 918
<212> TYPE: DNA
<213> ORGANISM: Artificial Sequence
<220> FEATURE:
<223> OTHER INFORMATION: Description of Artificial Sequence: Portion of
      Stratagene BIG BLUE lambda LIZ shuttle vector

<400> SEQUENCE: 1

```
tccccatctt gtctgcgaca gattcctggg ataagccaag ttcattttc ttttttcat      60 aaattgcttt aaggcgacgt gcgtcctcaa gctgctcttg tgttaatggt ttctttttg    120 tgctcatacg ttaaatctat caccgcaacg gataaatatc taacaccgtg cgtgttgact   180
attttacctc tggcggtgat aatggttgca tgtactaagg aggttgtatg gaacaacgca   240
taaccctgaa agattatgca atgcgctttg ggcaaaccaa gacagctaaa gatctcggcg   300
tatatcaaag cgcgatcaac aaggccattc atgcaggccg aaagattttt ttaactataa   360
acgctgatgg aagcgtttat gcggaagagg taaagccctt cccgagtaac aaaaaaacaa   420
cagcataaat aaccccgctc ttacacattc cagccctgaa aaagggcatc aaattaaacc   480
acacctatgg tgtatgcatt tatttgcata cattcaatca attgttatct aaggaaatac   540
ttacatatgg ttcgtgcaaa caaacgcaac gaggctctac gaatcgagag tgcgttgctt   600
aacaaaatcg caatgcttgg aactgagaag acagcggaag ctgtgggcgt tgataagtcg   660
cagatcagca ggtggaagag ggactggatt ccaaagttct caatgctgct tgctgttctt   720
gaatgggggg tcgttgacga cgacatggct cgattggcgc gacaagttgc tgcgattctc   780
accaataaaa aacgcccggc ggcaaccgag cgttctgaac aaatccagat ggagttctga   840
ggtcattact ggatctatca acaggagtca ttatgacaaa tacagcaaaa atactcaact   900
tcggcagagc taactttg                                                  918
```

<210> SEQ ID NO 2
<211> LENGTH: 97
<212> TYPE: PRT
<213> ORGANISM: Escherichia coli

<400> SEQUENCE: 2

```
Met Val Arg Ala Asn Lys Arg Asn Glu Ala Leu Arg Ile Glu Ser Ala
 1               5                  10                  15

Leu Leu Asn Lys Ile Ala Met Leu Gly Thr Glu Lys Thr Ala Glu Ala
            20                  25                  30

Val Gly Val Asp Lys Ser Gln Ile Ser Arg Trp Lys Arg Asp Trp Ile
        35                  40                  45

Pro Lys Phe Ser Met Leu Leu Ala Val Leu Glu Trp Gly Val Val Asp
    50                  55                  60

Asp Asp Met Ala Arg Leu Ala Arg Gln Val Ala Ala Ile Leu Thr Asn
65                  70                  75                  80

Lys Lys Arg Pro Ala Ala Thr Glu Arg Ser Glu Glu Ile Gln Met Glu
                85                  90                  95

Phe
```

```
<210> SEQ ID NO 3
<211> LENGTH: 446
<212> TYPE: DNA
<213> ORGANISM: Artificial Sequence
<220> FEATURE:
<223> OTHER INFORMATION: Description of Artificial Sequence:  cII gene

<400> SEQUENCE: 3
aaaaagggca tcaaattaaa ccacacctat ggtgtatgca tttatttgca tacattcaat      60
caattgttat ctaaggaaat acttacatat ggttcgtgca aacaaacgca acgaggctct     120
acgaatcgag agtgcgttgc ttaacaaaat cgcaatgctt ggaactgaga agacagcgga     180
agctgtgggc gttgataagt cgcagatcag caggtggaag agggactgga ttccaaagtt     240
ctcaatgctg cttgctgttc ttgaatgggg ggtcgttgac gacgacatgg ctcgattggc     300
gcgacaagtt gctgcgattc tcaccaataa aaaacgcccg gcggcaaccg agcgttctga     360
acaaatccag atggagttct gaggtcatta ctggatctat caacaggagt cattatgaca     420
aatacagcaa aaatactcaa cttcgg                                          446

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
gatgagttcg tgtccgtaca actgg                                            25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
ggttatcgaa atcagccaca gcgcc                                            25
```